(12) United States Patent
Wang et al.

(10) Patent No.: US 11,029,287 B2
(45) Date of Patent: *Jun. 8, 2021

(54) MULTI-FOCUS OPTICAL-RESOLUTION PHOTOACOUSTIC MICROSCOPY WITH ULTRASONIC ARRAY DETECTION

(71) Applicant: California Institute of Technology, Pasadena, CA (US)

(72) Inventors: Lihong Wang, Arcadia, CA (US); Liang Song, St. Louis, MO (US); Konstantin Maslov, Pasadena, CA (US); Bin Rao, St. Louis, MO (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/372,597

(22) Filed: Apr. 2, 2019

(65) Prior Publication Data

US 2019/0227038 A1 Jul. 25, 2019

Related U.S. Application Data

(60) Continuation of application No. 14/639,676, filed on Mar. 5, 2015, now Pat. No. 10,359,400, which is a (Continued)

(51) Int. Cl.
*G01N 29/24* (2006.01)
*A61B 5/00* (2006.01)
(Continued)

(52) U.S. Cl.
CPC ....... *G01N 29/2418* (2013.01); *A61B 5/0095* (2013.01); *G02B 21/36* (2013.01);
(Continued)

(58) Field of Classification Search
CPC .................... G01N 29/2418; A61B 5/0095
(Continued)

(56) References Cited

U.S. PATENT DOCUMENTS 4,029,756 A 6/1977 Gaafar
4,127,318 A 11/1978 Determann et al.
(Continued)

FOREIGN PATENT DOCUMENTS

CN 1883379 A 12/2006
EP 0012262 A1 6/1980
(Continued)

OTHER PUBLICATIONS

Ai et al., "Spectral-domain optical coherence tomography: Removal of autocorrelation using an optical switch", Applied Physics Letters, 2006, pp. 111115-1-111115-3, vol. 88.
(Continued)

*Primary Examiner* — Tarun Sinha
(74) *Attorney, Agent, or Firm* — Sheila Martinez-Lemke; Weaver Austin Villeneuve & Sampson LLP

(57) ABSTRACT

A probe for use with an imaging system, including a scanning device configured to receive a first light beam from a light source, a beam-divider configured to split the first light beam into a plurality of second light beams, and a focusing device configured to focus each of the second light beams on respective locations in an object of interest is disclosed.

18 Claims, 13 Drawing Sheets

Related U.S. Application Data division of application No. 13/369,558, filed on Feb. 9, 2012, now Pat. No. 8,997,572.

(60) Provisional application No. 61/442,148, filed on Feb. 11, 2011.

(51) Int. Cl.
  *G02B 26/10* (2006.01)
  *G02B 21/36* (2006.01)

(52) U.S. Cl.
  CPC .......... *G02B 26/105* (2013.01); *A61B 5/4064* (2013.01); *A61B 5/42* (2013.01); *A61B 5/441* (2013.01); *G01N 2291/028* (2013.01); *G01N 2291/106* (2013.01)

(58) Field of Classification Search
  USPC .......................................................... 73/606
  See application file for complete search history.

(56) References Cited

U.S. PATENT DOCUMENTS

| | | |
|---|---|---|
| 4,255,971 A | 3/1981 | Rosencwaig |
| 4,267,732 A | 5/1981 | Quate |
| 4,284,324 A | 8/1981 | Huignard et al. |
| 4,375,818 A | 3/1983 | Suwaki et al. |
| 4,385,634 A | 5/1983 | Bowen |
| 4,430,897 A | 2/1984 | Quate |
| 4,430,987 A | 2/1984 | Quate |
| 4,462,255 A | 7/1984 | Guess et al. |
| 4,468,136 A | 8/1984 | Murphy et al. |
| 4,489,727 A | 12/1984 | Matsuo et al. |
| 4,546,771 A | 10/1985 | Eggleton et al. |
| 4,596,254 A | 6/1986 | Adrian et al. |
| 4,687,304 A | 8/1987 | Piller et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,872,758 A | 10/1989 | Miyazaki et al. |
| 4,921,333 A | 5/1990 | Brody et al. |
| 4,929,951 A | 5/1990 | Small |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,194,723 A | 3/1993 | Cates et al. |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,329,817 A | 7/1994 | Garlick et al. |
| 5,331,466 A | 7/1994 | Van Saarloos |
| 5,345,938 A | 9/1994 | Nishiki et al. |
| 5,373,845 A | 12/1994 | Gardineer et al. |
| 5,414,623 A | 5/1995 | Lu et al. |
| 5,445,155 A | 8/1995 | Sieben |
| 5,465,722 A | 11/1995 | Fort et al. |
| 5,546,187 A | 8/1996 | Pepper et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,781,294 A | 7/1998 | Nakato et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,977,538 A | 11/1999 | Unger et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | Benett et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1 | 4/2003 | Stern |
| 6,564,087 B1 | 5/2003 | Pitris et al. |
| 6,567,688 B1 | 5/2003 | Wang |
| 6,590,830 B1 | 7/2003 | Garlick et al. |
| 6,626,834 B2 | 9/2003 | Dunnie et al. |
| 6,628,404 B1 | 9/2003 | Kelley et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,853,446 B1 | 2/2005 | Almogy et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1 | 10/2009 | Winchester, Jr. et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |
| 8,891,088 B2 | 11/2014 | Goldshmidt et al. |
| 8,997,572 B2 | 4/2015 | Wang et al. |
| 9,220,415 B2 | 12/2015 | Mandelis et al. |
| 9,234,841 B2 | 1/2016 | Wang et al. |
| 9,335,605 B2 | 5/2016 | Wang et al. |
| 9,528,966 B2 | 12/2016 | Wang et al. |
| 9,618,445 B2 | 4/2017 | Sun et al. |
| 10,359,400 B2 | 7/2019 | Wang et al. |
| 10,433,733 B2 | 10/2019 | Wang et al. |
| 10,448,850 B2 | 10/2019 | Wang et al. |

(56) References Cited

U.S. PATENT DOCUMENTS

| | | |
|---|---|---|
| 2001/0052979 A1 | 12/2001 | Tread et al. |
| 2002/0093637 A1 | 7/2002 | Yuan et al. |
| 2002/0173780 A1 | 11/2002 | Altshuler et al. |
| 2002/0176092 A1 | 11/2002 | Deck |
| 2003/0097066 A1 | 5/2003 | Shelby et al. |
| 2003/0160957 A1 | 8/2003 | Oldham et al. |
| 2003/0160967 A1 | 8/2003 | Houston et al. |
| 2004/0030255 A1 | 2/2004 | Alfano et al. |
| 2004/0039379 A1 | 2/2004 | Viator et al. |
| 2004/0082070 A1 | 4/2004 | Jones et al. |
| 2004/0254474 A1 | 12/2004 | Seibel et al. |
| 2005/0015002 A1 | 1/2005 | Dixon et al. |
| 2005/0028482 A1 | 2/2005 | Cable et al. |
| 2005/0143664 A1 | 6/2005 | Chen et al. |
| 2005/0154313 A1 | 7/2005 | Desilets et al. |
| 2005/0168749 A1 | 8/2005 | Ye et al. |
| 2005/0217381 A1 | 10/2005 | Falk |
| 2005/0234315 A1 | 10/2005 | Mayevsky et al. |
| 2005/0277824 A1 | 12/2005 | Aubry et al. |
| 2006/0055936 A1 | 3/2006 | Yun et al. |
| 2006/0058614 A1 | 3/2006 | Tsujita |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0247510 A1 | 11/2006 | Wiemker et al. |
| 2006/0264717 A1 | 11/2006 | Pesach et al. |
| 2007/0088206 A1 | 4/2007 | Peyman et al. |
| 2007/0093702 A1 | 4/2007 | Yu et al. |
| 2007/0213590 A1 | 9/2007 | Squicciarini |
| 2007/0213618 A1 | 9/2007 | Li et al. |
| 2007/0213693 A1 | 9/2007 | Plunkett |
| 2007/0282200 A1 | 12/2007 | Johnson et al. |
| 2007/0299341 A1 | 12/2007 | Wang et al. |
| 2008/0029711 A1 | 2/2008 | Viellerobe et al. |
| 2008/0037367 A1 | 2/2008 | Gross et al. |
| 2008/0088838 A1 | 4/2008 | Raicu et al. |
| 2008/0123083 A1 | 5/2008 | Wang et al. |
| 2008/0173093 A1 | 7/2008 | Wang et al. |
| 2008/0230717 A1 | 9/2008 | Ashkenazi et al. |
| 2009/0051900 A1 | 2/2009 | Moon et al. |
| 2009/0054763 A1* | 2/2009 | Wang .................... A61B 5/0059 600/425 |
| 2009/0088631 A1 | 4/2009 | Dietz et al. |
| 2009/0116518 A1 | 5/2009 | Patel et al. |
| 2009/0138215 A1 | 5/2009 | Wang et al. |
| 2009/0185191 A1 | 7/2009 | Boppart et al. |
| 2009/0227997 A1 | 9/2009 | Wang et al. |
| 2010/0079768 A1 | 4/2010 | Wang et al. |
| 2010/0134793 A1 | 6/2010 | Krishnamachari et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0268042 A1* | 10/2010 | Wang .................... A61B 5/0059 600/322 |
| 2010/0285518 A1 | 11/2010 | Viator et al. |
| 2010/0309466 A1 | 12/2010 | Lucassen et al. |
| 2010/0322497 A1 | 12/2010 | Dempsey et al. |
| 2011/0071402 A1 | 3/2011 | Masumura |
| 2011/0122416 A1 | 5/2011 | Yang et al. |
| 2011/0201914 A1 | 8/2011 | Wang et al. |
| 2011/0251515 A1 | 10/2011 | Leuthardt et al. |
| 2011/0275890 A1 | 11/2011 | Wang et al. |
| 2011/0282181 A1 | 11/2011 | Wang et al. |
| 2011/0282192 A1 | 11/2011 | Axelrod et al. |
| 2012/0070817 A1 | 3/2012 | Wang et al. |
| 2012/0074294 A1 | 3/2012 | Streuber et al. |
| 2012/0118052 A1 | 5/2012 | O'Donnell et al. |
| 2012/0204648 A1 | 8/2012 | Wang et al. |
| 2012/0275262 A1 | 11/2012 | Song et al. |
| 2012/0307250 A1 | 12/2012 | Wang et al. |
| 2013/0199299 A1 | 8/2013 | Wang et al. |
| 2013/0218002 A1 | 8/2013 | Kiraly |
| 2013/0245406 A1 | 9/2013 | Wang et al. |
| 2014/0009808 A1 | 1/2014 | Wang et al. |
| 2014/0142404 A1 | 5/2014 | Wang et al. |
| 2014/0356897 A1 | 12/2014 | Wang et al. |
| 2015/0005613 A1 | 1/2015 | Kim et al. |
| 2015/0185187 A1 | 7/2015 | Wang et al. |
| 2015/0245771 A1 | 9/2015 | Wang et al. |
| 2015/0272444 A1 | 10/2015 | Maslov et al. |
| 2015/0272446 A1 | 10/2015 | Wang et al. |
| 2015/0316510 A1 | 11/2015 | Fukushima et al. |
| 2016/0081558 A1 | 3/2016 | Wang et al. |
| 2016/0235305 A1 | 8/2016 | Wang et al. |
| 2016/0242651 A1 | 8/2016 | Wang et al. |
| 2016/0249812 A1 | 9/2016 | Wang et al. |
| 2016/0262628 A1 | 9/2016 | Wang et al. |
| 2016/0305914 A1 | 10/2016 | Wang et al. |
| 2016/0310083 A1 | 10/2016 | Wang et al. |
| 2016/0345886 A1 | 12/2016 | Wang et al. |
| 2017/0065182 A1 | 3/2017 | Wang et al. |
| 2017/0105636 A1 | 4/2017 | Wang et al. |
| 2017/0367586 A9 | 12/2017 | Wang et al. |
| 2018/0020920 A1 | 1/2018 | Ermilov et al. |
| 2018/0132728 A1 | 5/2018 | Wang et al. |
| 2019/0008444 A1 | 1/2019 | Wang et al. |
| 2019/0125583 A1 | 5/2019 | Wang et al. |
| 2019/0227038 A1 | 7/2019 | Wang et al. |
| 2019/0307334 A1 | 10/2019 | Wang et al. |
| 2020/0056986 A1 | 2/2020 | Wang et al. |
| 2020/0073103 A1 | 3/2020 | Wang et al. |
| 2020/0268253 A1 | 8/2020 | Wang et al. |
| 2020/0275846 A1 | 9/2020 | Wang et al. |
| 2020/0397523 A1 | 12/2020 | Gao et al. |
| 2021/0010976 A1 | 1/2021 | Wang et al. |

FOREIGN PATENT DOCUMENTS

| | | |
|---|---|---|
| EP | 0919180 A1 | 6/1999 |
| EP | 1 493 380 A1 | 1/2005 |
| JP | 05-126725 A | 5/1993 |
| JP | 2000292416 A | 10/2000 |
| JP | 2009-068977 A | 4/2009 |
| JP | 2010-017426 A | 1/2010 |
| JP | 2010/040161 A | 2/2010 |
| JP | 2012/143384 A | 8/2012 |
| JP | 2014124242 A | 7/2014 |
| JP | 2014/224806 A | 12/2014 |
| JP | 2016-101260 A | 6/2016 |
| JP | 6086718 B2 | 3/2017 |
| KR | 100946550 B1 * | 3/2010 |
| KR | 2017-0006470 A | 1/2017 |
| WO | 2006/111929 A1 | 10/2006 |
| WO | WO 2007/088709 A1 | 8/2007 |
| WO | 2007/148239 A2 | 12/2007 |
| WO | 2008/062354 A1 | 5/2008 |
| WO | 2008/100386 A2 | 8/2008 |
| WO | 2009/055705 A2 | 4/2009 |
| WO | 2010/048258 A1 | 4/2010 |
| WO | 2010/080991 A2 | 7/2010 |
| WO | WO 2011/060101 A2 | 5/2011 |
| WO | 2011/091360 A2 | 7/2011 |
| WO | 2011/127428 A2 | 10/2011 |
| WO | WO2012/035472 A1 | 3/2012 |
| WO | 2013/086293 A1 | 6/2013 |
| WO | WO2015/118881 A1 | 8/2015 |
| WO | WO2018/102446 A2 | 6/2018 |
| WO | WO 2018/209046 A1 | 11/2018 |

OTHER PUBLICATIONS

Allen et al., "Pulsed near-infrared laser diode excitation system for biomedical photoacoustic imaging", Optics Letters, 2006, pp. 3462-3464, vol. 31, No. 23.

Bell, "On the Production and Reproduction of Sound by Light", American Journal of Sciences, Third Series, Oct. 1880, pp. 305-324, vol. XX.

Calasso et al., "Photoacoustic Point Source", Physical Review Letters, 2001, pp. 3550-3553, vol. 86, No. 16.

(56) References Cited

OTHER PUBLICATIONS

Cheong et al., "A Review of the Optical Properties of Biological Tissues", IEEE Journal of Quantum Electronics, 1990, pp. 2166-2185, vol. 26, No. 12.
D'Andrea et al., "Time-resolved optical imaging through turbid media using a fast data acquisition system based on a gated CCD camera", Journal of Physics D: Applied Physics, 2003, pp. 1675-1681, vol. 36.
de Boer et al., "Improved signal-to-noise ratio in spectral-domain compared with time-domain optical coherence tomography", Optics Letters, 2003, pp. 2067-2069, vol. 28, No. 21.
Diebold et al., "Photoacoustic "Signatures" of Particulate Matter: Optical Production of Acoustic Monopole Radiation", Science, New Series, 1990, pp. 101-104, vol. 250, No. 4977.
Diebold et al., "Photoacoustic Monopole Radiation in One, Two, and Three Dimensions", Physical Review Letters, 1991, pp. 3384-3387 and Figs. 1 and 2, vol. 26, No. 24.
Dunn et al., "Transport-based image reconstruction in turbid media with small source-detector separations", Optics Letters, 2000, pp. 1777-1779, vol. 25, No. 24.
Extended European Search Report from European Patent Application No. 08842292.8, dated Dec. 17, 2013, 8 pgs.
Fan et al., "Development of a laser photothermoacoustic frequency-swept system for subsurface imaging: Theory and experiment", J. Acoust. Soc. Am., 2004, pp. 3523-3533, vol. 116, No. 6.
Fang et al., "Photoacoustic Doppler Effect from Flowing Small Light-Absorbing Particles", Physical Review Letters, 2007, pp. 184501 1-184501 4, vol. 99.
Fercher et al., "Measurement of intraocular distances by backscattering spectral interferometry", Optics Communications, 1995, pp. 43-48, vol. 117.
Foster et al., "Advances in Ultrasound Biomicroscopy", Ultrasound in Medicine and Biology, 2000, pp. 1-27, vol. 26, No. 1.
Gibson et al., "Recent advances in diffuse optical imaging", Physics in Medicine and Biology, 2005, pp. R1-R43, vol. 50.
Guittet et al., "In Vivo High-Frequency Ultrasonic Characterization of Human Dermis", IEEE Transactions on Biomedical Engineering, 1999, pp. 740-746, vol. 46, No. 6.
Hebden et al., "Enhanced time-resolved imaging with a diffusion model of photon transport", Optics Letters, 1994, pp. 311-313, vol. 19, No. 5.
Hee et al., "Femtosecond transillumination tomography in thick tissues", Optics Letters, 1993, pp. 1107-1109, vol. 18, No. 13.
Hillman et al., "Laminar optical tomography: demonstration of millimeter-scale depth-resolved imaging in turbid media", Optics Letters, 2004, pp. 1650-1652, vol. 29, No. 14.
Hoelen et al., "Three-dimensional photoacoustic imaging of blood vessels in tissue", Optics Letters, 1998, pp. 648-650, vol. 23, No. 8.
Huang et al., "Optical Coherence Tomography", Science, New Series, 1991, pp. 1178-1181, vol. 254, No. 5035.
Huber et al., "Three-dimensional and C-mode OCT imaging with a compact, frequency swept laser source at 1300 nm", Optics Express, 2005, pp. 10523-10538, vol. 13, No. 26.
ISR and Written Opinion from related International Application No. PCT/US2008/081167, dated Apr. 22, 2009; 7 pgs.
ISR and Written Opinion from related International Application No. PCT/US2009/061435, dated Mar. 29, 2010; 10 pgs.
ISR and Written Opinion from related International Application No. PCT/US2010/020488, dated Aug. 31, 2010; 10 pgs.
ISR and Written Opinion from related International Application No. PCT/US2011/022253, dated Sep. 22, 2011; 8 pgs.
ISR and Written Opinion from related International Application No. PCT/US2011/031823, dated Dec. 26, 2011; 8 pgs.
ISR and Written Opinion from related International Application No. PCT/US2012/068403, dated Mar. 19, 2013; 10 pgs.
Karamata et al., "Multiple scattering in optical coherence tomography. I. Investigation and modeling", Journal Optical Society of America, 2005, pp. 1369-1379, vol. 22, No. 7.
Kolkman et al., "In Vivo Photoacoustic Imaging of Blood Vessels Using an Extreme-Narrow Aperture Sensor", IEEE Journal of Selected Topics in Quantum Electronics, 2003, pp. 343-346, vol. 9, No. 2.
Kruger et al., "Thermoacoustic computed tomography—technical considerations", Medical Physics, 1999, pp. 1832-1837, vol. 26, No. 9.
Kruger et al., "Breast Cancer in Vivo: Contrast Enhancement with Thermoacoustic CT at 434 MHz—Feasibility Study", Radiology, 2000, pp. 279-283, vol. 216, No. 1.
Kruger et al., "Thermoacoustic computed tomography using a conventional linear transducer array", Medical Physics, 2003, pp. 856-860, vol. 30, No. 5.
Kruger et al., "Thermoacoustic Optical Molecular Imaging of Small Animals", Molecular Imaging, 2003, pp. 113-123, vol. 2.
Ku et al., "Scanning thermoacoustic tomography in biological tissue", Medical Physics, 2000, pp. 1195-1202, vol. 27, No. 5.
Ku et al., "Scanning microwave-induced thermoacoustic tomography: Signal, resolution, and contrast", Medical Physics, 2001, pp. 4-10, vol. 28, No. 1.
Ku et al., "Multiple-bandwidth photoacoustic tomography", Physics. Med. Biol., 2004, pp. 1329-1338, vol. 49, No. 7.
Ku et al., "Deeply penetrating photoacoustic tomography in biological tissues enhanced with an optical contrast agent", Optics Letters, 2005, pp. 507-509, vol. 30, No. 5.
Ku et al., "Thermoacoustic and Photoacoustic Tomography of Thick Biological Tissues Toward Breast Imaging", Technology in Cancer Research & Treatment, 2005, pp. 559-566, vol. 4, No. 5.
Leitgeb et al., "Performance of fourier domain vs. time domain optical coherence tomography", Optics Express, 2003, pp. 889-894, vol. 11, No. 8.
Li et al., "Optical coherence computed tomography", Applied Physics Letters, 2007, pp. 141107-1-141107-3, vol. 91.
Li et al., "Simultaneous Molecular and Hypoxia Imaging of Brain Tumors in Vivo Using Spectroscopic Photoacoustic Tomography", Proceedings of the IEEE, 2008, pp. 481-489, vol. 96, No. 3.
Manohar et al., "Initial Results of in vivo non-invasive cancer imaging in the human breast using near-infrared photoacoustics", Optics Express, 2007, pp. 12277-12285, vol. 15, No. 19.
Maslov et al., "In vivo dark-field reflection-mode photoacoustic microscopy", Optics Letters, 2005, pp. 625-627, vol. 30, No. 6.
Maslov et al., "Photoacoustic imaging of biological tissue with intensity-modulated continuous-wave laser", Journal of Biomedical Optics, 2008, pp. 024006 1-024006 5, vol. 13, No. 2.
Mishra et al., "Development and comparison of the DTM, the DOM and the FVM formulations for the short-pulse laser transport through a participating medium", International Journal of Heat and Mass Transfer, 2006, pp. 1820-1832, vol. 49.
Morgner et al., "Spectroscopic optical coherence tomography", Optics Letters, 2000, pp. 111-113, vol. 25, No. 2.
Murray et al., "High-sensitivity laser-based acoustic microscopy using a modulated excitation source", Applied Physics Letters, 2004, pp. 2974-2976, vol. 85, No. 14.
Nakajima et al., "Three-Dimensional Analysis and Classification of Arteries in the Skin and Subcutaneous Adipofascial Tissue by Computer Graphics Imaging", Plastic and Reconstructive Surgery, 1998, pp. 748-760, vol. 102, No. 3.
Cannatta et al., "Development of a 353-MHz piezo-composite ultrasound array for medical imaging" IEEE Transaction on Ultrasonics, Ferroelectrics and Frequency Control, 2006, pp. 224-236, vol. 53.
Ermilov et al., "Laser optoacoustic imaging system for detection of breast cancer", Journal of Biomedical Optics, 2009, vol. 14.
Erpelding et al., "Sentinel Lymph Nodes in the Rat: Noninvasive Photoacoustic and US Imaging with a Clinical US System", Radiology, 2010, pp. 102-110, vol. 256.
Hu et al., "Label-free photoacoustic ophthalmic angiography", Optics Letters, 2010, pp. 1-3, vol. 35, No. 1.
Kim et al., "In vivo molecular photoacoustic tomography of melanomas targeted by bioconjugated gold nanocages", Acs Nano, 2010, pp. 4559-4564, vol. 4, No. 8.
Kruger et al., "Photoacoustic Ultrasound (Paus)—Reconstruction Tomography", Medical Physics, 1995, pp. 1605-1609, vol. 22.

(56) References Cited

OTHER PUBLICATIONS

Ku et al., "Imaging of tumor angiogenesis in rat brains in vivo by photoacoustic tomography", Applied Optics, 2005, pp. 700-775, vol. 44, No. 5.
Maslov et al., "Optical-resolution photoacoustic microscopy for in vivo imaging of single capillaries", Optical Letters, 2008, pp. 929-931, vol. 33, No. 9.
Niederhauser et al., "Combined ultrasound and optoacoustic system for real-time high contrast vascular imaging in vivo", IEEE Transactions on Medical Imaging, 2005, pp. 436-440, vol. 24.
Song et al., "Fast 3-D dark-field reflection-mode photoacoustic microscopy in vivo with a 30-MHz ultrasound linear array", Journal of Biomedical Optics, 2008, vol. 13.
Song et al., "Section-illumination photoacoustic microscopy for dynamic 3-D imaging of microcirculation in vivo", Optics Letters, 2010, vol. 35.
Wang, "Multiscale photoacoustic microscopy and computed tomography", Nature Photonics, 2009, pp. 503-509, vol. 3.
Wang et al., "Intravascular Photoacoustic Imaging", IEEE Journal of Selected Topics in Quantum Electronics, 2010, pp. 588-599, vol. 16.
Wang et al., "Noninvasive laser-induced photoacoustic tomography for structural and functional in vivo imaging of the brain", Nature Biiotechnology, 2003, pp. 803-806, vol. 21, No. 7.
Yang et al., "Optical coherence and Doppler tomography for monitoring tissue changes induced by laser thermal therapy—an in vivo feasibility study", Review of Scientific Instruments, 2003, pp. 437-440, vol. 74, No. 1.
Yang et al., "Novel biomedical imaging that combines intravascular ultrasound (IVUS) and optical coherence tomography (OCT)", IEEE International Ultrasonics Symposium Proceedings, 2008, pp. 1769-1772.
Yao et al., "Monte Carlo simulation of an optical coherence tomography signal in homogeneous turbid media", Phys. Med. Biol., 1999, pp. 2307-2320, vol. 44.
Yaqoob et al., "Methods and application areas of endoscopic optical coherence tomography", Journal of Biomedical Optics, 2006, pp. 063001-1 through 063001-19, vol. 11, No. 6.
Yodh et al., "Spectroscopy and Imaging With Diffusing Light", Physics Today, Mar. 1995, pp. 34-40.
Yodh et al., "Functional Imaging with Diffusing Light", Biomedical Photonics Handbook, 2003, Chapter 21, 45 pgs., CRC Press, Boca Raton.
Zeff et al., "Retinotopic mapping of adult human visual cortex with high-density diffuse optical tomography", Proceedings of the National Academy of Sciences, 2007, pp. 12169-12174, vol. 104, No. 29.
Zemp et al., "Realtime photoacoustic microscopy in vivo with 30-MHz ultrasonic array transducer", Optics Express, 2008, pp. 7915-7928, vol. 16.
Zhang et al., "Functional photoacoustic microscopy for high-resolution and noninvasive in vivo imaging", Nature Biotechnology, 2006, pp. 848-851, vol. 24, No. 7.
Zhang et al., "In vivo imaging of subcutaneous structures using functional photoacoustic microscopy", Nature Protocols, 2007, pp. 797-804, vol. 2, No. 4.
Zhang et al., "Intrinsic Functional Relations Between Human Cerebral Cortex and Thalamus", J Neurophysiol, 2008, pp. 1740-1748, vol. 100.
Zharov et al., "In vivo photoacoustic flow cytometry for monitoring of circulating single cancer cells and contrast agents", Optics Letters, 2006, pp. 3623-3625, vol. 31, No. 24.
Zou et al., "BOLD response to visual stimulation in survivors of childhood cancer", NeuroImage, 2005, pp. 61-69, vol. 24.
Final Office Action from related U.S. Appl. No. 13/450,793 dated Nov. 22, 2013; 22 pgs.
Non-Final Office Action from related U.S. Appl. No. 13/450,793 dated Mar. 24, 2014; 22 pgs.
Nelson et al., "Imaging Glioblastoma Multiforme", the Cancer Journal, 2003, pp. 134-145, vol. 9, No. 2.
Office Action from related U.S. Appl. No. 13/574,994, dated Aug. 26, 2014; 10 pgs.
Office Action from related U.S. Appl. No. 13/574,994, dated Mar. 17, 2014; 9 pgs.
Notice of Allowance from related U.S. Appl. No. 12/739,589, dated Feb. 5, 2013; 9 pgs.
Office Action from related U.S. Appl. No. 12/739,589, dated Jul. 19, 2012; 9 pgs.
Notice of Allowance from related U.S. Appl. No. 12/254,643, dated Nov. 22, 2010; 8 pgs.
Office Action from related U.S. Appl. No. 12/254,643, dated Aug. 6, 2010; 9 pgs.
Office Action from related U.S. Appl. No. 11/625,099, dated Nov. 1, 2010; 11 pgs.
Office Action from related U.S. Appl. No. 11/625,099, dated Apr. 20, 2010; 11 pgs.
Office Action from related U.S. Appl. No. 13/450,793, dated Jun. 5, 2013; 20 pgs.
Office Action from related U.S. Appl. No. 13/637,897, dated Aug. 1, 2014; 7 pgs.
Notice of Allowance from related U.S. Appl. No. 12/568,069, dated Feb. 22, 2013; 7 pgs.
Office Action from related U.S. Appl. No. 12/568,069, dated Dec. 21, 2012; 10 pgs.
Office Action from related U.S. Appl. No. 12/568,069, dated Sep. 18, 2012; 14 pgs.
Office Action from related U.S. Appl. No. 12/568,069, dated Mar. 29, 2012; 10 pgs.
Office Action from related U.S. Appl. No. 13/143,832, dated Apr. 18, 2014; 14 pgs.
Office Action from related U.S. Appl. No. 13/125,522, dated Jul. 17, 2014; 10 pgs.
Office Action from related U.S. Appl. No. 13/125,522, dated May 23, 2013; 10 pgs.
Office Action from related U.S. Appl. No. 13/125,522, dated Jan. 22, 2013; 8 pgs.
Oraevsky et al., "Laser Optoacoustic Tomography of Layered Tissues: Signal Processing", SPIE, 1997, pp. 59-70, vol. 2979.
Oraevsky et al., "Laser Opto-Acoustic Imaging of the Breast: Detection of Cancer Angiogenesis", Proc. SPIE, 1999, pp. 352-363, vol. 3597, No. 56.
Oraevsky et al., "Ultimate Sensitivity of Time-Resolved Opto-Acoustic Detection", Biomedical Optoacoustics, Proceedings of SPIE, 2000, pp. 228-239, vol. 3916.
Oraevsky et al., "Optoacoustic Tomography", Biomedical Photonics Handbook, 2003, pp. 1-40, CRC Press LLC, USA.
Petrov et al., "Optoacoustic, Noninvasive, Real-Time, Continuous Monitoring of Cerebral Blood Oxygenation: An in Vivo Study in Sheep", Anesthesiology, 2005, pp. 69-75, vol. 102, No. 1.
Potter et al., "Capillary Diameter and Geometry in Cardiac and Skeletal Muscle Studied by Means of Corrosion Casts", Microvascular Research, 1983, pp. 68-84, vol. 25.
Robert et al., "Fabrication of focused poly (vinylidene fluoride-trifluoroethylene) P (VDF-TrFE) copolymer 40-50 MHz ultrasound transducers on curved surfaces", Journal of Applied Physics, 2004, pp. 252-256, vol. 96, No. 1.
Saager et al., "Direct characterization and removal of interfering absorption trends in two-layer turbid media", J. Opt. Soc. Am. A, 2005, pp. 1874-1882, vol. 22, No. 9.
Savateeva et al., "Noninvasive detection and staging of oral cancer in vivo with confocal opto-acoustic tomography", Proceedings of SPIE, 2000, pp. 55-66, vol. 3916.
Schmidt et al., "A 32-channel time-resolved instrument for medical optical tomography", Review of Scientific Instruments, 2000, pp. 256-265, vol. 71, No. 1.
Schroeter et al., "Spontaneous slow hemodynamic oscillations are impaired in cerebral microangiopathy", Journal of Cerebral Blood Flow & Metabolism, 2005, pp. 1675-1684, vol. 25.
Sethuraman et al., "Development of a combined intravascular ultrasound and photoacoustic imaging system", Proc. of SPIE, 2006, pp. 60860E-1 through 60860E-10, vol. 6086.

(56) References Cited

OTHER PUBLICATIONS

Sethuraman et al., "Intravascular photoacoustic imaging of atherosclerotic plaques: ex vivo study using a rabbit model of atherosclerosis", Proc. of SPIE, 2007, pp. 643729-1 through 643729-9, vol. 6437.
Sheth et al., "Columnar Specificity of Microvascular Oxygenation and vol. Responses: Implications for Functional Brain Mapping", the Journal of Neuroscience, 2004, pp. 634-641, vol. 24, No. 3.
Shmueli et al., "Low-frequency fluctuations in the cardiac rate as a source of variance in the resting-state fMRI BOLD signal", NeuroImage, 2007, pp. 306-320, vol. 38.
Siphanto et al., "Imaging of Small Vessels Using Photoacoustics: An in Vivo Study", Lasers in Surgery and Medicine, 2004, pp. 354-362, vol. 35.
Steinbrink et al., "Illuminating the BOLD signal: combined fMRI-fNIRS studies", Magnetic Resonance Imaging, 2006, pp. 495-505, vol. 24.
Stern, "In vivo evaluation of microcirculation by coherent light scattering", Nature, 1975, pp. 56-58, vol. 254.
Tam, "Applications of photoacoustic sensing techniques", Reviews of Modern Physics, 1986, pp. 381-431 and Figs. 16, 26 and 32, vol. 58, No. 2.
Tearney et al., "Scanning single-mode fiber optic catheter-endoscope for optical coherence tomography", Optics Letters, 1996, pp. 543-545, vol. 21, No. 7.
Tran et al., "In vivo endoscopic optical coherence tomography by use of a rotational microelectromechanical system probe", Optics Letters, 2004, pp. 1236-1238, vol. 29, No. 11.
Van Essen et al., "An Integrated Software Suite for Surface-based Analyses of Cerebral Cortex", Journal of the American Medical Informatics Association, 2001, pp. 443-459, vol. 8, No. 5.
Viator et al., "Design and testing of an endoscopic photoacoustic probe for determination of treatment depth after photodynamic therapy", SPIE Proceedings in Biomedical Optoacoustics II, 2001, pp. 16-27, vol. 4256.
Wang et al., "Ballistic 2-D Imaging Through Scattering Walls Using an Ultrafast Optical Kerr Gate", Science, 1991, pp. 769-771, vol. 253.
Wang et al., "MCML—Monte Carlo modeling of light transport in multi-layered tissues", Computer Methods and Programs in Biomedicine, 1995, pp. 131-146, vol. 47.
Wang et al., "Three-dimensional laser-induced photoacoustic tomography of mouse brain with the skin and skull intact", Optics Letters, 2003, pp. 1739-1741, vol. 28, No. 19.
Wang et al., "Noninvasive photoacoustic angiography of animal brains in vivo with near-infrared light and an optical contrast agent", Optics Letters, 2004, pp. 730-732, vol. 29, No. 7.
Wang et al., "Biomedical Optics, Principles and Imaging", 2007, Wiley-Interscience, a John Wiley & Sons, Inc., Hoboken, New Jersey, US, 7 pgs.
Xu et al., "Photoacoustic imaging in biomedicine", Review of Scientific Instruments, 2006, pp. 041101 1-041101 22, vol. 77.
Xu et al., "Time Reversal Ultrasound Modulated Optical Tomography Using a BSO Phase Conjugate Mirror", poster presented at SPIE Conference 7177 on Jan. 26, 2009; 3 pgs.
Yadlowsky et al., "Multiple scattering in optical coherence microscopy", Applied Optics, 1995, pp. 5699-5707, vol. 34, No. 25.
Final Office Action from related U.S. Appl. No. 13/125,522, dated Oct. 29, 2014.
Office Action dated Aug. 26, 2015 issued in U.S. Appl. No. 13/125,522.
Final Office Action dated Mar. 3, 2016 issued in U.S. Appl. No. 13/125,522.
Notice of Allowance dated Sep. 19, 2016 issued in U.S. Appl. No. 13/125,522.
Office Action from related U.S. Appl. No. 13/450,793, dated Aug. 1, 2014 (21 pages).
Notice of Allowance dated Nov. 17, 2015 from U.S. Appl. No. 13/574,994.
Office Action dated Jan. 20, 2015, from U.S. Appl. No. 14/026,577.
Final Office Action dated Sep. 30, 2015, from U.S. Appl. No. 14/026,577.
Notice of Allowance dated Jan. 5, 2016, from U.S. Appl. No. 14/026,577.
Office Action dated Nov. 13, 2017, from U.S. Appl. No. 15/148,685.
Final Office Action dated Sep. 24, 2018, from U.S. Appl. No. 15/148,685.
Notice of Allowance dated May 16, 2019, from U.S. Appl. No. 15/148,685.
Office Action from related U.S. Appl. No. 14/164,117, dated Dec. 11, 2015 (18 pages).
Office Action dated Dec. 13, 2019 issued in U.S. Appl. No. 15/037,468.
Notice of Allowance dated Mar. 23, 2020 issued in U.S. Appl. No. 15/037,468.
Amendment and Request for Continued Examination dated Nov. 25, 2019 in U.S. Appl. No. 14/436,581.
Final Office Action dated May 24, 2019 issued in U.S. Appl. No. 14/436,581.
Office Action dated Apr. 3, 2020 issued in U.S. Appl. No. 14/436,581.
Office Action dated Jun. 20, 2014 issued in U.S. Appl. No. 13/369,558.
Notice of Allowance dated Jul. 29, 2014 issued in U.S. Appl. No. 13/369,558.
Notice of Allowance dated Dec. 5, 2014 issued in U.S. Appl. No. 13/369,558.
Office Action dated Apr. 21, 2017 issued in U.S. Appl. No. 14/639,676.
Final Office Action dated Nov. 15, 2017 issued in U.S. Appl. No. 14/639,676.
Office Action dated May 31, 2018 issued in U.S. Appl. No. 14/639,676.
Notice of Allowance dated Dec. 12, 2018 issued in U.S. Appl. No. 14/639,676.
The International Search Report and Written Opinion dated Mar. 27, 2014 issued in Application No. PCT/US2013/065594.
International Search Report of International Application No. PCT/US2014/066437, dated Feb. 26, 2015, 3 pages.
Partial European Search Report issued for European Application No. 17159220.7, dated Aug. 23, 2017 (9 pages).
Final Office Action from related Japanese Patent Application No. JP 2010-531281, dated Mar. 11, 2014, (5 pages).
International Search Report and Written Opinion dated Dec. 2, 2019, issued in Application No. PCT/US2019/046574.
International Search Report and Written Opinion dated Dec. 23, 2019, issued in Application No. PCT/US2019/049594.
Abdelmohsen, et al., "Micro- and nano-motors for biomedical applications," J. Mater. Chem. B 2, (2014) pp. 2395-2408.
Alomair, et al., "In vivo high angular resolution diffusion-weighted imaging of mouse brain at 16.4 Tesla," PloS One 10, Jun. 25, 2015, e0130133, pp. 1-17.
Aubry J.-F., et al., "Experimental demonstration of noninvasive transskull adaptive focusing based on prior computed tomography scans," J. Acoust. Soc. Am. 113(1), 84-93 (2003). (Year: 2003).
Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.
Baker, M. J. et al., "Using Fourier transform IR spectroscopy to analyze biological materials," Nat. Protoc. 9, 1771-1791 (2014).
Bansil, et al., "The biology of mucus: Composition, synthesis and organization" Adv. Drug Deliv. Rev. 124, (2018) pp. 3-15.
Beaven, G. H. & Holiday, E. R., "Ultraviolet absorption spectra of proteins and amino acids," Adv. Protein Chem 7, 319-386 (1952).
Bellinger, et al., "Oral, ultra-long-lasting drug delivery: Application toward malaria elimination goals" Sci Transl. Med. 8(365), Nov. 16, 2016, 365ra157, pp. 1-25. <doi:10.1126/scitranslmed.aag2374>.
Bioucas-Dias, J.M. and Figueiredo, M.A.T. "A new TwIST: two-step iterative shrinkage/thresholding algorithms for image restoration," IEEE Trans. Image Process. 16, 2992-3004 (Dec. 2007).
Brenner, et al., "Computed Tomography—an Increasing Source of Radiation Exposure" N. Engl. J. Med 357;22, Nov. 29, 2007, pp. 2277-2284.
Celli, J. P., et al., "Helicobacter pylori moves through mucus by reducing mucin viscoelasticity," Proc. Natl. Acad. Sci. U. S. A. 106, (2009) pp. 14321-14326.

(56) References Cited

OTHER PUBLICATIONS

Chan, et al., "New opportunities in micro- and macro-attenuated total reflection infrared spectroscopic imaging: spatial resolution and sampling versatility," Appl. Spectrosc. 57, 381-389 (2003).

Cheng, J.-X. et al., "Vibrational spectroscopic imaging ofliving systems: an emerging platform for biology and medicine," Science, vol. 350 aaa8870, No. 6264, Nov. 27, 2015, pp. 1054-1063.

Chourasia, et al., "Design and Development of Multiparticulate System for Targeted Drug Delivery to Colon," Drug Delivery, 11:3, (2004) pp. 201-207.

Cox, B., Beard, P., "Photoacoustic tomography with a single detector in a reverberant cavity" J. Acoust. Soc. Am. 125, 1426 (Mar. 2009).

Cui, Y., et al. "Transferring-conjugated magnetic silica PLGA nanoparticles loaded with doxorubicin and paclitaxel for brain glioma treatment," Biomaterials 34, (2013) pp. 8511-8520.

Danielli, et al., "Label-free photoacoustic nanoscopy," Journal of Biomedical Optics, vol. 19, No. 8, Aug. 2014, pp. 086006-1-086006-10.

Dazzi, A. et al., "AFM-IR: technology and applications in nanoscale infrared spectroscopy and chemical imaging," Chem. Rev. 117, 5146-5173 (2017).

Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.

de Avila, et al., "Micromotor-enabled active drug delivery for in vivo treatment of stomach infection" Nat. Commun. 8: 272, (2017) pp. 1-9.

de Zerda, et al., "Family of enhanced photoacoustic imaging agents for high-sensitivity and multiplexing studies in living mice," ACS Nano 6(6), Jun. 26, 2012, pp. 4694-4701.

Diem, M. et al., "Molecular pathology via IR and Raman spectral imaging." Journal of Biophotonics, vol. 6, No. 11-12 (2013) pp. 855-886. <doi:10.1002/jbio.201300131>.

Diem, M., et al., "A decade of vibrational micro-spectroscopy of human cells and tissue (1994-2004)†," Analyst, Oct. 2004, vol. 129, No. 10, pp. 880-885. <doi:10.1039/b408952a>.

Draeger, C., Fink, M., "One-channel time reversal of elastic waves in a chaotic 2D-silicon cavity," Phys. Rev. Lett. 79, 407-410 (Jul. 21, 1997).

Eghtedari, et al., "High Sensitivity of in Vivo Detection of Gold Nanorods Using a Laser Optoacoustic Imaging System," Nano Letters, vol. 7, No. 7, 2007, pp. 1914-1918.

Evans, et al., "Coherent Anti-Stokes Raman Scattering Microscopy: Chemical Imaging for Biology and Medicine," Annual Review of Analytical Chemistry 1, (2008), pp. 883-909.

Fan, et al., "Sub-Cellular Resolution Delivery of a Cytokine via Precisely Manipulated Nanowires" Nat. Nanotechnol. 5(7), Jul. 2010, 545-551. <doi:10.1038/nnano.2010.104>.

Fernandez, D. C., Bhargava, R., Hewitt, S. M. & Levin, I. W., "Infrared spectroscopic imaging for histopathologic recognition," Nat. Biotechnol. 23, 469-474 (2005).

Fujita, K., et al., "Confocal multipoint multiphoton excitation microscope with microlens and pinhole arrays," Opt. Comm. 174, 7-12 (Jan. 15, 2000).

Furstenberg, et. al., "Chemical Imaging using Infrared Photothermal Microspectroscopy," in Proceedings of SPIE Defense, Security, and Sensing (eds Druy, M.A. & Crocombe, R. A.) 837411 (SPIE, 2012).

Gaihre, et al., "Gelatin-coated magnetic iron oxide nanoparticles as carrier system: Drug loading and in vitro drug release study," Int. J. Pharm. 365, (2009) pp. 180-189.

Gao, et al., "Single-shot compressed ultrafast photography at one hundred billion frames per second," Nature 516(7529) 74-77 (Dec. 4, 2014).

Gao, et al., "A review of snapshot multidimensional optical imaging: measuring photon tags in parallel" Phys Rep. 616, Feb. 29, 2016, pp. 1-37. <doi:10.1016/j.physrep.2015.12.004>.

"Gao, et al., "Artificial micromotors in the mouse's stomach: A step toward in vivo use of synthetic motors," ACS Nano 9, (2015) pp. 117-123."

Gong, L. et al., "Breaking the diffraction limit by saturation in stimulated-Raman-scattering microscopy: a theoretical study," Phys. Rev. A 90, 13818 (2014).

Griffiths, P., "Fourier transform infrared spectrometry," Science 21, 297-302 (1983).

Guggenheim, et al., "Ultrasensitive planoconcave optical microresonators for ultrasound sensing", Nat. Photon. 11, 714-721 (2017).

Guo, et al., "Calibration-free absolute quantification of optical absorption coefficients using acoustic spectra in three-dimensional photoacoustic microscopy of biological tissue" Opt Lett. 2010; 35(12): 2067-2069. <doi:10.1364/OL.35.002067>.

Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).

Haas, J. et al., "Advances in Mid-Infrared Spectroscopy for Chemical Analysis," Annu. Rev. Anal. Chem. 9 (2016) pp. 45-68.

Hai, et al., "Near-infrared optical-resolution photoacoustic microscopy", Opt. Lett. 39, 5192-5195 (Sep. 1, 2014).

Hai, et al., "High-throughput, label-free, single-cell photoacoustic microscopy of intratumoral metabolic heterogeneity," Nature Biomedical Engineering 3(5) 381-391 (May 2019).

Hong, et al., "Simple Method to Produce Janus Colloidal Particles in Large Quantity" Langmuir 22, (2006) pp. 9495-9499.

Hu, C., et al., "Soft Micro- and Nanorobotics," Annu. Rev. Control. Robot. Auton. Syst. 1, (2018) pp. 53-75.

Hu, W., et al., "Small-scale soft-bodied robot with multimodal locomotion," Nature 554, 81-85, (2018).

Hu, S. et al., "Three-dimensional optical-resolution photoacoustic microscopy," Journal of Visualized Experiments 51 (2011).

Huang, et al., "Aberration correction for transcranial photoacoustic tomography of primates employing adjunct image data," Journal of Biomedical Optics, vol. 17, No. 6, Jun. 2012, pp. 066016-1 to 066016-8.

Imai, T. et al., "High-throughput ultraviolet photoacoustic microscopy with multifocal excitation," Journal of Biomedical Optics 23(3), 036007 (Mar. 15, 2018).

Ing, R. K., Quieffin, N., Catheline, S., Fink, M., "In solid localization of finger impacts using acoustic time-reversal process," Appl. Phys. Lett. 87, 204104 (Nov. 14, 2005).

Ji, M. et al., "Detection of human brain tumor infiltration with quantitative stimulated Raman scattering microscopy," Sci. Transl. Med 7, 309ra163 (2015).

Ji, T. et al. "Preparation, Characterization, and Application of Au-Shell/Polystyrene Beads and Au-hell/Magnetic Beads" Adv. Mater. 13(16), Aug. 2001, pp. 1253-1256.

Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.

Kirch, J., et al., "Optical tweezers reveal relationship between microstructure and nanoparticle penetration of pulmonary mucus," Proc. Natl. Acad. Sci. 109, (2012) pp. 18355-18360.

Knoll, B. & Keilmann, F., "Near-field probing of vibrational absorption for chemical microscopy," Nature 399, 134-137 (1999).

Kole, M. R., et al., "Discrete frequency infrared microspectroscopy and imaging with a tunable quantum cascade laser," Anal. Chem. 84, 10366-10372 (2012).

Koziolek, et al., "Navigating the human gastrointestinal tract for oral drug delivery: Uncharted waters and new frontiers," Adv. Drug Delivery Rev. 101, (2016) pp. 75-88.

Kruger, et al., "Thermoacoustic CT: imaging principles," Proc. SPIE 3916, (2000) pp. 150-160.

Kunitz, M., "Crystalline desoxyribonuclease; isolation and general properties; spectrophotometric method for the measurement of desoxyribonuclease activity," the Journal General Physiology, vol. 33, Mar. 20, 1950, pp. 349-362. <URL:http://doi.org./10.1085/jgp.33.4.349>.

(56) References Cited

OTHER PUBLICATIONS

Lai, S. et al., "Mucus-penetrating nanoparticles for drug and gene delivery to mucosal tissues," Adv. Drug Deliv. Rev. 61(2), Feb. 27, 2009, pp. 158-171. <doi:10.1016/j.addr.2008.11.002>.

Lai, P. et al., "Photoacoustically guided wavefront shaping for enhanced optical focusing in scattering media," Nature Photonics 9 126-132 (Jan. 19, 2015).

Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035002-6.

Larina, et al., Real-time optoacoustic monitoring of temperature in tissues: Journal of Physics D: Applied Physics, vol. 38, (2005) pp. 2633•-2639.

Lasch, et al., "FT-IR spectroscopic investigations of single cells on the subcellular level," Vibr. Spectrosc. 28, 147-157 (2002).

Laser Institute of America, "American National Standard for the safe use of lasers," American National Standard Institute (ANSI Z136.1-2007 Revision of ANSI Z136.1-2000).

Leal, et al., "Physicochemical properties of mucus and their impact on transmucosal drug delivery," Int. J. Pharm. 532, (2017) pp. 555-572.

Lewis, E. N. et al., "Fourier transform spectroscopic imaging using an infrared focal-Plane array detector," Anal. Chem. 67, 3377-3381 (1995).

Li, et al., "An Enteric Micromotor Can Selectively Position and Spontaneously Propel in the Gastrointestinal Tract," ACS Nano. 10(10), Oct. 25, 2016, pp. 9536-9542. <doi:10.1021/acsnano.6b04795>.

Li, et al., "Autonomous Collision-Free Navigation of Microvehicles in Complex and Dynamically Changing Environments" ACS Nano, 11, (2017) pp. 9268-9275.

Li, G., et al., "Reflection-mode multifocal optical-resolution photoacoustic microscopy," J. Biomed. Opt. 18, 030501 (Feb. 12, 2013).

Li, L., et al., "Small near-infrared photochromic protein for photoacoustic multi-contrast imaging and detection of protein interactions in vivo," Nature Communications 9(1) 2734 (Jul. 16, 2018).

Li, et al., "Single-impulse panoramic photoacoustic computed tomography of small-animal whole-body dynamics at high spatiotemporal resolution," Nat Biomed Eng. 1(5) May 2017, pp. 1-11. <doi:10.1038/s41551-017-0071>.

Li, J. et al., "Micro/Nanorobots for Biomedicine: Delivery, Surgery, Sensing, and Detoxification" Sci Robot, 2(4), Mar. 15, 2017, pp. 1-20. <doi:10.1126/scirobotics.aam6431>.

Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.

Li, et al., "Snapshot photoacoustic topography through an ergodic relay for high-throughput imaging of optical absorption," Nature Photonics, Jan. 20, 2020. <URL:https://doi.org/10.1038/s41566-019-0576-2>.

Li, Z., et al., "Super-resolution far-field infrared imaging by photothermal heterodyne imaging," the Journal of Physical Chemistry B, vol. 121 (2017) pp. 8838-8846.

Li, Z., et al., "Super-resolution imaging with mid-IR photothermal microscopy on the single particle level," in Proceedings of SPIE Physical Chemistry of Interfaces and Nano-materials XIV, vol. 9549, Aug. 20, 2015, pp. 954912-1-954912-8.

Liang, et al., "Single-shot real-time femtosecond imaging of temporal focusing," Light-Science & Applications 7(1) 42 (Aug. 8, 2018).

Liang, et al., "Single-shot real-time video recording of a photonic Mach cone induced by a scattered light pulse," Science Advances 3(1) e1601814 (Jan. 20, 2017).

Liang, et al., "Single-shot ultrafast optical imaging," Optica 5(9) 1113-1127 (Sep. 2018).

Lin, et al., "Single-breath-hold photoacoustic computed tomography of the breast," Nature Communications 9(1) 2352 (Jun. 15, 2018).

Liu, et al., "Optical focusing deep inside dynamic scattering media with near-infrared time-reversed ultrasonically encoded (TRUE) light," Nature Communications 6 5409 (Jan. 5, 2015).

Liu, et al., "Label-free cell nuclear imaging by Gruneisen relaxation photoacoustic microscopy" Opt Lett. Feb. 15, 2018; 43(4), (2018) pp. 947-950.

Lovell, et al., "Porphysome nanovesicles generated by porphyrin bilayers for use as multimodal biophotonic contrast agents," Nature Materials 10(4) 324-32 (Mar. 20, 2011).

Lu, F., et al., "Tip-enhanced infrared nanospectroscopy via molecular expansion force detection," Nat. Photon. 8, 307-312 (2014).

Lu, F.-K. et al., "Label-free DNA imaging in vivo with stimulated Raman scattering microscopy," Proc. Natl Acad Sci. USA 112, 11624-11629 (2015).

Ma, et al., "Time-reversed adapted-perturbation (TRAP) optical focusing onto dynamic objects inside scattering media," Nature Photonics 8(12) 931-936 (Nov. 2, 2014).

Medina-Sanchez, et al., "Medical microbots need better imaging and control," Nature 545, 406-408. (2017) pp.

Michaelian, Kirk H. Photoacoustic IR spectroscopy: instrumentation, applications and data analysis. Pub: John Wiley & Sons; Dec. 1, 2010 <Preface Only>.

Miller, et al., "Synchrotron-based biological microspectroscopy: From the mid-infrared through the far-infrared regimes," Journal of Biological Physics 29, 219-230 (2003).

Montaldo, et al., "Building three-dimensional images using time-reversal chaotic cavity", IEEE Trans. Ultrason. Ferroelectr. Freq. Control 52, pp. 1489-1497 (2005).

Nasiriavanaki, et al., "High-resolution photoacoustic tomography of resting-state functional connectivity in the mouse brain," Proceedings of the National Academy of Sciences 111(1) 21-26 (Jan. 7, 2014).

Nasse, M. J. et al., "High-resolution Fourier-transform infrared chemical imaging with multiple synchrotron beams," Nat. Methods 8, 413-416 (2011).

Nowak, D. et al., "Nanoscale chemical imaging by photoinduced force microscopy," Sci. Adv. 2, Mar. 25, 2016, e1501571, pp. 1-9.

Ntziachristos, V., "Going deeper than microscopy: the optical imaging frontier in biology" Nature Methods vol. 7, No. 8, Aug. 2010, pp. 603-614.

Patel, et al., "Pulsed optoacoustic spectroscopy of condensed matter," Rev. Mod. Phys., vol. 53 (1981) pp. 517-550.

Paxton, et al., "Catalytic nanomotors: Autonomous movement of striped nanorods," J. Am. Chem. Soc. 126, 13424-13431 (2004).

Prati, et al., "New advances in the application of FTIR microscopy and spectroscopy for the characterization of artistic materials," Accounts of Chemical Research, vol. 43, (2010) pp. 792-801.

Prevedel, et al., "Simultaneous whole-animal 3D imaging of neuronal activity using light-field microscopy," Nat. Methods 11, 727-730 (Jul. 2014).

Quickenden, et al., "The ultraviolet absorption spectrum ofliquid water," J Chem. Phys. 72, 4416-4428 (1980).

Razansky, et al., "Multispectral opto-acoustic tomography of deep-seated fluorescent proteins in vivo," Nature Photonics 3, (2009) pp. 412-417.

Rockley, M.G., "Fourier-transformed infrared photoacoustic spectroscopy of polystyrene film," Chem. Phys. Lett. 68, 455-456 (1979).

Rosenblum, et al., "Progress and challenges towards targeted delivery of cancer therapeutics" Nat. Commun. 9, (2018) 1410, pp. 1-12.

Sanchez, et al., "Chemically powered micro- and nanomotors," Angew. Chem. Int. Ed. 54, (2015) pp. 1414-1444.

Sakadzic, et al., "Correlation transfer and diffusion of ultrasound-modulated multiply scattered light," Physical Review Letters 96(16) 163902-(1-4) (Apr. 28, 2006).

Schambach, et al., "Application of micro-CT in small animal imaging" Methods, vol. 50, No. 1, Jan. 2010, pp. 2-13.

Servant, et al., "Controlled in Vivo Swimming of a Swarm of Bacteria-Like Microrobotic Flagella," Advanced Materials 27, (2015) pp. 2981-2988.

(56) References Cited

OTHER PUBLICATIONS

Sezer, et al., "Review of magnesium-based biomaterials and their applications," J. Magnesium Alloys 6, (2018) pp. 23-43.
Shah, J. et al, "Photoacoustic imaging and temperature measurement for photothermal cancer therapy," Journal of Biomedical Optics, vol. 13, No. 3, (May/Jun. 2008) pp. 034024-1-034024-9.
Shi, J., et al., "High-resolution, high-contrast mid-infrared imaging of fresh biological samples with ultraviolet-localized photoacoustic microscopy," Nature Photonics 13 609-615 (May 2019).
Silva, et al., "Toward Label-Free Super-Resolution Microscopy," ACS Photon. 3, 79-86 (2016).
Sim, et al., "In vivo Microscopic Photoacoustic Spectroscopy for Non-Invasive Glucose Monitoring Invulnerable to Skin Secretion Products," Sci. Rep. 8, 1059 (2018).
Sitti, M., "Miniature soft robots-road to the clinic," Nat. Rev. Mater, 3, (2018) pp. 74-75.
Smith, et al., "Beyond C, H, O, and Ni analysis of the elemental composition of U.S. FDA approved drug architectures," J. Med. Chem. 57, pp. 9764-9773 (2014).
Sommer, A. J., et al., "Attenuated total internal reflection infrared mapping microspectroscopy using an imaging microscope," Appl. Spectrosc. 55, 252-256 (2001).
Song et al., "Multi-focal optical-resolution photoacoustic microscopy in vivo." NIH Public Access Author Manuscript, May 13, 2011. pp. 1-7.
"Soppimath, et al., "Microspheres as floating drug-delivery systems to increase gastric retention of drugs," Drug Metab. Rev. 33, (2001) pp. 149-160."
Tay, et al., "Magnetic Particle Imaging Guided Heating in Vivo using Gradient Fields for Arbitrary Localization of Magnetic Hyperthermia Therapy" ACS Nano. 12(4), Apr. 24, 2018, pp. 3699-3713. <doi:10.1021/acsnano.8b00893>.
Treeby B. E., et al., "Photoacoustic tomography in absorbing acoustic media using time reversal," Inverse Probl. (2010) 26(11), pp. 1-20.
Tu, et al., "Self-propelled supramolecular nanomotors with temperature-responsive speed regulation," Nat. Chem. 9, 480 (2016).
Velasco, E., "Ultrafast Camera Takes 1 Trillion Frames Per Second of Transparent Objects and Phenomena" [Webpage] Caltech, California Institute of Technology, Jan. 17, 2020, pp. 1-2. <URL:https://www.eurekalert.org/pub_releases/2020-01/ciot-uct012120.php>.
Vilela, et al., "Medical imaging for the tracking of micromotors," ACS Nano 12, (2018) pp. 1220-1227.
Wang, et al., "Fabrication of micro/nanoscale motors" Chem. Rev. 115, (2015) pp. 8704-8735.
Wang, L. et al., "Grueneisen relaxation photoacoustic microscopy," Physical Review Letters 113 174301 (Oct. 24, 2014).
Wang, L. V & Yao, J., "A practical guide to photoacoustic tomography in the life sciences," Nat. Methods 13, 627-638 (Jul. 28, 2016).
Wang, L. V.; "Mechanisms of ultrasonic modulation of multiply scattered coherent light: an analytic model," Physical Review Letters 87(4) 043903-(1-4) (Jul. 23, 2001).
Wang, L. V.; "Prospects of photoacoustic tomography," Medical Physics 35(12), Nov. 19, 2008, pp. 5758-5767.
Wang, L., et al., "Single-cell label-free photoacoustic flowoxigraphy in vivo," Proceedings of the National Academy of Sciences 110(15) 5759-5764 (Apr. 9, 2013).
Wang, L., et al., "Ultrasonically encoded photoacoustic flowgraphy in biological tissue," Physical Review Letters 111(20), 204301 (Nov. 15, 2013).
Wang, L.V., Hu, S. "Photoacoustic Tomography: in vivo imaging from organelles to organs," Science 335, 1458-1462 (Mar. 23, 2012).
Wang, et al., "Nano/microscale motors: biomedical opportunities and challenges," ACS Nano 6, (2012) pp. 5745-5751.
Wetzel, et al., "Imaging molecular chemistry with infrared microscopy," Science, New Series, vol. 285, No. 5431, Aug. 20, 1999, pp. 1224-1225.

Wong, T. et al., "Fast label-free multilayered histology-like imaging of human breast cancer by photoacoustic microscopy," Sci. Adv. 3, 1602168 (May 17, 2017).
Wong, T. et al., "Label-free automated three-dimensional imaging of whole organ by microtomy-assisted photoacoustic microscopy," Nat. Comm. 8, (Nov. 9, 2017).
Wu, Z., et al., "A microrobotic system guided by photoacoustic computed tomography for targeted navigation in intestines in vivo," Science Robotics 4(32) eaax0613 (Jul. 24, 2019).
Wu, D., et al., "In vivo Mapping of Macroscopic Neuronal Projections in the Mouse Hippocampus using High-resolution Diffusion MRI," Neuroimage 125, Jan. 15, 2016, pp. 84-93.
Xia, J., et al., "Photoacoustic tomography: principles and advances," Electromagn. Waves 147, 1 (2014; available in PMC Jan. 30, 2015).
Xia, J., et al., "Wide-field two-dimensional multifocal optical-resolution photoacoustic-computed microscopy," Opt. Lett. 38(24), Dec. 15, 2013, pp. 5236-5239.
Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.
Xu, M. H.; Wang, L. V.; "Time-domain reconstruction for thermoacoustic tomography in a spherical geometry," IEEE Transactions on Medical Imaging 21(7) 814-822 (Jul. 2002).
Xu, M. H.; Wang, L. V.; "Universal back-projection algorithm for photoacoustic computed tomography," Physical Review E 71(1) 016706-(1-7) (Jan. 19, 2005).
Xu, S., et al., "Thermal expansion of confined water," Langmuir 25, 5076-5083 (2009).
Xu, X. et al., "Time-reversed ultrasonically encoded optical focusing into scattering media," Nature Photonics 5(3) 154-157 (Jan. 16, 2011).
Xu, Y.; Wang, L. V.; "Time reversal and its application to tomography with diffracting sources," Physical Review Letters 92(3) 033902-(1-4) (Jan. 23, 2004).
Yan, et al., "Multifunctional biohybrid magnetite microrobots for imaging-guided therapy" Yan et al., Sci. Robot. 2, eaaq1155, Nov. 22, 2017, pp. 1-14.
Yang, J. M. et al., "Simultaneous functional photoacoustic and ultrasonic endoscopy of internal organs in vivo," Nature Medicine 18(8) 1297-1303 (Aug. 2012).
Yang, J., et al., "Motionless volumetric photoacoustic microscopy with spatially invariant resolution," Nature Communications 8(1) 780 (Oct. 3, 2017).
Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.
Yang, et al., "The grand challenges of science robotics," Science Robotics 3, Jan. 31, 2018, eaar7650, pp. 1-14.
Yao, et al., "Absolute photoacoustic thermometry in deep tissue," Opt. Lett. 38, 5228-5231 (2013).
Yao, et al., "In vivo label-free photoacoustic microscopy of cell nuclei by excitation of DNA and RNA," Opt. Lett. 35, 4139-4141 (2010).
Yao, et al., "Optimal ultraviolet wavelength for in vivo photoacoustic imaging of cell nuclei," J Biomed. Opt. 17, 056004 (2012).
Yao, et al., "Photoimprint photoacoustic microscopy for three-dimensional label-free sub-diffraction imaging," Physical Review Letters 112(1) 014302 (Jan. 10, 2014).
Yao, L. et al., "Multiscale photoacoustic tomography using reversibly switchable bacterial phytochrome as near-infrared photochromic probe," Nature Methods 13(1) 67-73 (Jan. 2016).
Yao, L. et al., "High-speed label-free functional photoacoustic microscopy of mouse brain in action," Nat. Methods 12(5), 407-410 (May 12, 2015).
Yao, L. et al., "Photoacoustic microscopy: superdepth, superresolution, and superb contrast", IEEE Pulse 6, 34-7 (May 13, 2015).
Yavuz, M. S., et al., "Gold nanocages covered by smart polymers for controlled release with near-infrared light," Nature Materials 8(12) 935-939 (Nov. 1, 2009).
Yin, et al., "Agarose particle-templated porous bacterial cellulose and its application in cartilage growth in vitro" Acta Biomater. Jan. 12, 2015, pp. 129-138. <doi:10.1016/j.actbio.2014.10.019>.

(56) References Cited

OTHER PUBLICATIONS

Zhang, C., et al., "Coherent Raman scattering microscopy in biology and medicine," Annu. Rev. Biomed. Eng. 17, 415-445 (2015).
Zhang, D. et al., "Depth-resolved mid-infrared photothermal imaging of living cells and organisms with submicrometer spatial resolution," Sci. Adv. 2, e1600521 (2016).
U.S. Appl. No. 16/798,204, filed Feb. 21, 2020, Wang et al.
U.S. Appl. No. 16/806,796, filed Mar. 2, 2020, Wang et al.
U.S. Appl. No. 16/946,496, filed Jun. 24, 2020, Gao et al.
Notice of Allowance dated Oct. 28, 2020 issued in U.S. Appl. No. 15/037,468.
Office Action dated Oct. 3, 2018 issued in U.S. Appl. No. 14/436,581.
International Search Report and Written Opinion dated Aug. 31, 2020, issued in Application No. PCT/US2020/019368.
International Search Report and Written Opinion dated Oct. 14, 2020, issued in Application No. PCT/US2020/07174.
International Search Report dated Aug. 9, 2018 issued in Application No. PCT/US2018/032007.
Written Opinion of the International Searching Authority dated Aug. 9, 2018 issued in Application No. PCT/US2018/032007.
International Preliminary Report on Patentability dated Nov. 12, 2019 issued in PCT/US2018/032007.
Karshalev, E. et al., "Micromotor Pills as a Dynamic Oral Delivery Platform" American Chemical Society Nano, 2018, vol. 12, No. 8, pp. 8397-8405 <DOI: 10.1021/acsnano.8b03760>.
Kuppusami, S. et al., "Parylene Coatings in Medical Devices and Implants: A Review" Universal Journal of Biomedical Engineering, 2015, vol. 3, No. 2, pp. 9-14 <DOI: 10.13189/ujbe.2015.030201>.
Li, J. et al., "Micromotors Spontaneously Neutralize Gastric Acid for pH-Responsive Payload Release" Angewandte Chemie International Edition, vol. 56, No. 8, 2017, pp. 2156-2161. <DOI: 10.1002/anie.201611774>.
Wang, B. et al., "Recent progress on micro- and nano-robots: towards in vivo tracking and localization" Quantitative Imaging in Medicine and Surgery, 2018, vol. 8, No. 5, pp. 461-479. <DOI: 10.21037/qims.2018.06.07>.
Yang, J.M., et al., "Focusing light inside live tissue using reversibly switchable bacterial phytochrome as a genetically encoded photochromic guide star" Science Advances 5(12) (2019) pp. 1-9.
U.S. Appl. No. 16/611,939, filed Nov. 8, 2019, Wang et al.
Notice of Allowance dated Jan. 26, 2021 issued in U.S. Appl. No. 14/436,581.
Arridge, et al., "Accelerated high-resolution photoacoustic tomography via compressed sensing," ArXiv Prepr. ArXiv160500133, 2016, pp. 8908-8940.
Cox, et al., "Artifact trapping during time reversal photoacoustic imaging for acoustically heterogeneous media," IEEE Trans. Med. Imaging, vol. 29, No. 2, (2010) pp. 387-396.
Deàn-Ben, et al., "Functional optoacoustic neuro-tomography for scalable whole-brain monitoring of calcium indicators," Light Sci. Appl., vol. 5, No. 12, p. e16201, 2016, pp. 1-7.
Dean-Ben, et al., "Portable spherical array probe for volumetric real-time optoacoustic imaging at centimeter-scale depths," Opt. Express, vol. 21, No. 23, 2013, pp. 28062-28071.
Deserno, M., "How to generate equidistributed points on the surface of a sphere," Polym. Ed, p. 99, 2004, p. 1.
Han, Y. et al., "Three-dimensional optoacoustic reconstruction using fast sparse representation," Opt. Lett., vol. 42, No. 5, (2017) pp. 979-982.
Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.
Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.
R. A. Kruger, et al., "Dedicated 3D photoacoustic breast imaging," Med. Phys., vol. 40, No. 11, 2013, pp. 113301-1-113301-8.
Maslov, et al., "Label-free automated three-dimensional imaging of whole organs by microtomy-assisted photoacoustic microscopy," Nature Communications 8(1) 1386 (2017), pp. 1-8.
Matthews, et al., "Parameterized Joint Reconstruction of the Initial Pressure and Sound Speed Distributions for Photoacoustic Computed Tomography," SIAM J. Imaging Sci., vol. 11, No. 2, (2018) pp. 1560-1588.
Matsumoto, et al., "Label-free photoacoustic imaging of human palmar vessels: a structural morphological analysis," Sci. Rep., vol. 8, No. 1, (2018) p. 786.
Mitsuhashi, et al., "A forward-adjoint operator pair based on the elastic wave equation for use in transcranial photoacoustic computed tomography," SIAM J. Imaging Sci., vol. 10, No. 4, 2017, pp. 2022-2048.
Mitsuhashi, et al., "Investigation of the far-field approximation for modeling a transducer's spatial impulse response in photoacoustic computed tomography," Photoacoustics, vol. 2, No. 1, 2014, pp. 21-32.
Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.
Pramanik, M., "Improving tangential resolution with a modified delayand-sum reconstruction algorithm in photoacoustic and thermoacoustic tomography," JOSA A, vol. 31, No. 3, (2014) pp. 621-627.
Scholte, et al., "On spatial sampling and aliasing in acoustic imaging" 12th Intern. congress on sound and vibration, Lisbon, Portugal (2005) pp. 1-8.
Schoeder, et al., "Optoacoustic image reconstruction: the full inverse problem with variable bases," Proc. R. Soc. A, vol. 474, No. 2219, (2018) pp. 1-20.
Treeby, et al., "k-Wave: MATLAB toolbox for the simulation and reconstruction of photoacoustic wave fields," J. Biomed. Opt., vol. 15, No. 2, Mar./Apr. 2010, pp. 021314.
Treeby, et al., "Advanced photoacoustic image reconstruction using the k-Wave toolbox," in Photons Plus Ultrasound: Imaging and Sensing 2016, 2016, vol. 9708, p. 97082P.
Tzoumas, et al., "Eigenspectra optoacoustic tomography achieves quantitative blood oxygenation imaging deep in tissues," Nat. Commun., vol. 7, 2016, pp. 1-10.
Wang et al., "Biomedical optics: principles and imaging," Section 12.5; Photoacoustic Tomography, John Wiley & Sons (2012) pp. 288-290.
Wang, K. et al., "Investigation of iterative image reconstruction in three-dimensional optoacoustic tomography," Phys. Med. Biol., vol. 57, No. 17, 2012, p. 5399-5423.
Xu, et al., "Exact frequency-domain reconstruction for thermoacoustic tomography-II: Cylindrical geometry," IEEE Trans. Med. Imaging, vol. 21, No. 7, (2002) pp. 829-833.
Zhou, et al., "Tutorial on photoacoustic tomography," J. Biomed. Opt., vol. 21, No. 6, Jun. 2016, pp. 061007-1-061007-14.
U.S. Appl. No. 17/090,752, filed Nov. 5, 2020, Wang et al.

* cited by examiner

MULTI-FOCUS OPTICAL-RESOLUTION PHOTOACOUSTIC MICROSCOPY WITH ULTRASONIC ARRAY DETECTION

CROSS-REFERENCE TO RELATED APPLICATION

This application is a continuation of prior U.S. patent application Ser. No. 14/639,676, filed on Mar. 5, 2015, which is a divisional of prior U.S. patent application Ser. No. 13/369,558, filed on Feb. 9, 2012, the entirety of which are incorporated herein in their entirety. U.S. application Ser. No. 13/369,558 claims the benefit of U.S. Provisional Application No. 61/442,148 filed Feb. 11, 2011, which is also incorporated herein in its entirety.

STATEMENT REGARDING FEDERALLY SPONSORED RESEARCH & DEVELOPMENT

This invention was made with government support under grants R01 EB000712 and U54 CA136398, both awarded by the U.S. National Institutes of Health. The government has certain rights in the invention.

BACKGROUND

The ability to image microstructures, such as the microvascular network in the skin, the GI tract, or the brain cortex, and to monitor physiological functions of tissue is invaluable. One of the promising technologies for accomplishing this objective is photoacoustic microscopy. Current high-resolution optical imaging techniques, such as optical coherence tomography, can image up to approximately one transport mean free path (about 1 mm) into biological tissue. However, these techniques are insensitive to optical absorption that is related to important biochemical information. Other well-known techniques, such as confocal microscopy and multi-photon microscopy, often involve the introduction of exogenous dyes, which, with a few notable exceptions, have relatively high toxicity. In addition, acoustic microscopic imaging and spectroscopy systems are sensitive to acoustic impedance variations only, which have low contrast for early-stage cancer and provide little functional information about biological tissue except flow. In contrast, photoacoustic wave magnitude is, within certain bounds, linearly proportional to the optical absorption contrast; thus photoacoustic spectral measurement can be performed to gain functional (physiological) information such as the local blood oxygenation level.

BRIEF DESCRIPTION

In one aspect, an imaging method is provided the includes receiving a first light beam from a light source; splitting the first light beam into a plurality of second light beams using a beam-divider; focusing the plurality of second light beams on respective locations in an object of interest using a focusing device; and receiving the acoustic signals from the object of interest using an ultrasonic transducer array. The plurality of second light beams may cause the object of interest to emit acoustic signals. The plurality of second light beams and acoustic signals may be coaxially aligned on opposite sides of the object of interest in a transmission mode. The method may further include coaxially merging the plurality of second light beams and the acoustic signals using an optical-acoustic beam combiner. Coaxially merging the plurality of second light beams and the acoustic signals may include passing the plurality of second light beams through the optical-acoustic beam combiner to the focusing device and reflecting the acoustic signals entering the optical-acoustic beam combiner toward the ultrasonic transducer array. Coaxially merging the plurality of second light beams and the acoustic signals may include reflecting the plurality of second light beams entering the optical-acoustic beam combiner toward the focusing device and passing the acoustic signals through the optical-acoustic beam combiner to the ultrasonic transducer array. The method may further include reflecting the first light beam toward the beam-divider using a movable scanning mirror. The first light beam may be reflected in a raster scanning pattern. The method may further include generating an image based on the acoustic signals. The plurality of second light beams may be formed as a linear array. The acoustic signals may be received by a linear ultrasonic transducer array. The plurality of second light beams may be formed as a 2D array. The acoustic signals may be received by a 2D ultrasonic transducer array.

BRIEF DESCRIPTION OF THE DRAWINGS

The embodiments described herein may be better understood by referring to the following description in conjunction with the accompanying drawings.

DETAILED DESCRIPTION

Figure 1:
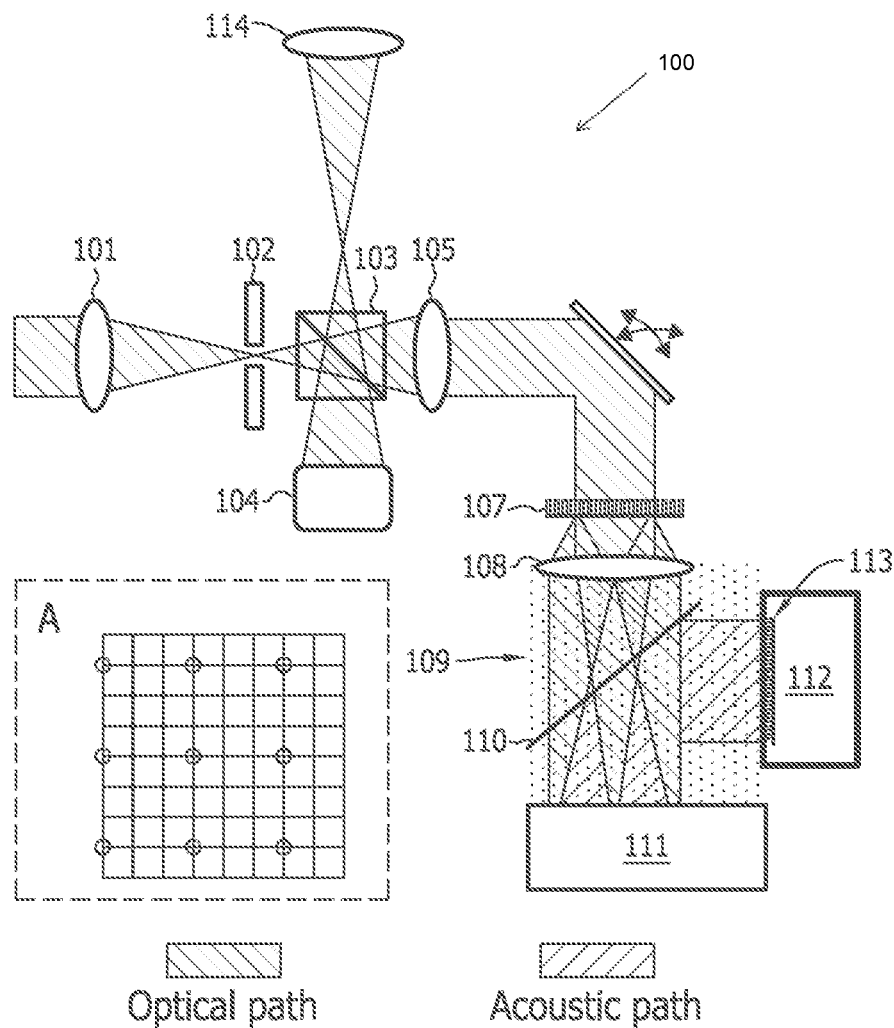
FIG. 1 is a diagram of a photoacoustic probe of an imaging system in accordance with one embodiment of the present disclosure, where a 2D transmission grating and an optically transparent acoustic reflector are employed.

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

To facilitate the understanding of this disclosure, a number of terms are defined below. Terms defined herein have meanings as commonly understood by a person of ordinary skill in the areas relevant to the present disclosure. Terms such as "a," "an" and "the" are not intended to refer to only a singular entity, but include the general class of which a specific example may be used for illustration. The terminology herein is used to describe specific embodiments of the disclosure, but their usage does not delimit the disclosure, except as outlined in the claims.

To be consistent with the commonly used terminology, whenever possible, the terms used herein will follow the definitions recommended by the Optical Society of America (OCIS codes).

In some embodiments, the term "photoacoustic microscopy" refers to a photoacoustic imaging technology that detects pressure waves generated by light absorption in the volume of a material (such as biological tissue) and propagated to the surface of the material. In other words, photoacoustic microscopy is a method for obtaining images of the optical contrast of a material by detecting acoustic or pressure waves traveling from the object. As used herein, the term "photoacoustic microscopy" includes detection of the pressure waves that are still within the object.

In some embodiments, the terms "reflection mode" and "transmission mode" refer to a laser photoacoustic microscopy system that employs the detection of acoustic or pressure waves transmitted from the volume of their generation to the optically irradiated surface and a surface that is opposite to, or substantially different from, the irradiated surface, respectively.

In some embodiments, the term "multi-focus 1D array illumination" refers to optical illumination for photoacoustic excitation with a one-dimensional array of focused pulsed laser beams.

In some embodiments, the term "multi-focus matrix illumination" refers to optical illumination for photoacoustic excitation using a two-dimensional array (matrix) of focused pulsed laser beams.

In some embodiments, the term "linear ultrasonic array" refers to a one-dimensional array of ultrasonic transducers, with which the two-dimensional (2D) in-plane spatial distributions and strength of ultrasonic (photoacoustic) sources can be reconstructed based on the time-resolved signals arriving at the array.

In some embodiments, the term "matrix ultrasonic array" refers to a two-dimensional array of ultrasonic transducers, with which the 3D spatial distributions and strength of photoacoustic sources can be reconstructed based on the time-resolved signals arriving at the array. Ultrasonic transducers generally refer to all types of ultrasonic wave detection devices including devices utilizing optical interferometers to sense ultrasonic waves.

In some embodiments, the term "diffraction limited resolution" refers to the best possible resolution by focusing light within the limitations imposed by diffraction.

In some embodiments, the term "photoacoustic emissions" refers to the pressure waves produced by light absorption.

In some embodiments, the term "B-scan image" refers to a cross-sectional two-dimensional image in the plane containing the acoustic axis.

In some embodiments, the term "integrated focusing assembly" refers to an integrated assembly including optical focusing components, an ultrasonic array, and the coupling devices between them.

In some embodiments, the term "photoacoustic reconstruction" refers to a signal processing technique used to reconstruct a photoacoustic B-scan image from received signals.

Embodiments of the present disclosure provide methods, systems, and apparatus for high-speed, optical-resolution photoacoustic imaging using multi-focus optical illumination in conjunction with ultrasonic array detection. Specifically, embodiments of the present disclosure use multiple focused pulsed laser beams to produce a rapid local temperature rise at multiple optical foci from absorption of the pulsed light. The temperature rise leads to a transient thermal expansion, resulting in photoacoustic emissions, which are detected by a high-frequency ultrasonic array to reconstruct an image. The image signal amplitude is related to the optical absorption and Grueneisen parameter. With each laser pulse, the multi-focus illumination excites photoacoustic waves from multiple sites, which the ultrasonic array detects simultaneously. The use of the ultrasonic array with photoacoustic reconstruction allows the separation of signals from the multiple optical illumination sites as close as the lateral resolution of the ultrasonic array. Fundamentally different from simply combining multiple assemblies of a single optical focusing element and a single ultrasonic transducer, this approach has enabled us to position optical foci much closer to each other.

Compared with previously existing optical-resolution photoacoustic microscopy, embodiments of the present disclosure significantly reduce the range or area of scanning for 2D or 3D imaging, respectively, by up to two to three orders, depending on the number of illumination spots. As a result, rapid scanning can be used to produce 2D or 3D photoacoustic imaging with optical resolution at high speed—even in real time. For example, using multi-focus matrix illumination in conjunction with matrix ultrasonic array detection, a 3D photoacoustic image can be produced by rapidly scanning the illumination over a small area comparable in size with the lateral resolution of the ultrasonic array. In fact, even with a simplified design using 1D array illumination in conjunction with linear ultrasonic array detection, the multi-focus optical-resolution photoacoustic microscopy device demonstrates a significant improvement in imaging speed over previously existing optical-resolution photoacoustic microscopy devices.

At an ultrasonic frequency suitable for ~1 millimeter (mm) penetration in soft tissue, the optical diffraction limited spatial resolution can be two orders of magnitude finer than the acoustically defined counterpart. In addition, in comparison with a conventional broad light illumination, the confined illumination significantly reduces the background arising from the interference of photoacoustic waves from various targets within the illumination volume. Due to the minimal scanning requirement of the present disclosure, a handheld 3D imaging device can also be made, which could be particularly useful for clinical applications such as intraoperative surgery. Moreover, the high imaging speed of the present disclosure is critical for clinical practice in order to reduce motion artifacts, patient discomfort, cost, and risks associated with minimally invasive procedures such as endoscopy.

The embodiments described in detail herein employ a tunable dye laser pumped by an Nd:YLF laser as the irradiation source. The laser pulse duration is on the order of several nanoseconds. The pulse repetition rate, which is controlled by an external triggering signal, can be as high as a few kilohertz (kHz), without significant degradation of the output energy. In other embodiments, a plurality of sources of penetrating radiation, which can be confined to or concentrated in a small volume within the object, can be used. Such sources include, but are not limited to, pulsed lasers, flash lamps, other pulsed electromagnetic sources, particle beams, or their intensity-modulated continuous-wave counterparts.

To provide multi-focus optical illumination for photoacoustic excitation, the embodiments described in detail herein use either a microlens array or a transmission grating in conjunction with an objective lens; for photoacoustic signal detection, an ultrasonic array is used. However, the present disclosure includes any realization of light focusing using any kind of mirrors, lenses, fibers, and/or diaphragms that can produce multi-focus illumination confined to the field of view of a linear or matrix ultrasonic array. In scattering biological tissue, the system can image ~1 mm deep, with axial and lateral resolutions determined by the ultrasonic bandwidth and the optical focusing, respectively. With an oscillating mirror, the present disclosure provides rapid optical scanning for 3D imaging, enabling optical-resolution photoacoustic microscopy at high speed.

The imaging procedure described herein is one of the possible embodiments specifically aimed at medical and biological applications. The optical absorption contrast of the present disclosure is complementary to other contrasts that can be obtained from purely optical or ultrasonic imaging technologies, and can be used for diagnostic, monitoring, or research purposes. The main applications of the technology include, but are not limited to, the imaging of arteries, veins, and pigmented tumors (such as melanomas) in vivo in humans or animals. The present disclosure can use the spectral properties of intrinsic optical contrast to monitor blood oxygenation, blood volume (total hemoglobin concentration), and even the metabolic rate of oxygen; it can also use the spectral properties of a variety of dyes or other contrast agents to obtain additional functional or molecular information. In short, the present disclosure is capable of functional and molecular imaging. In addition, the present disclosure can be used to monitor possible tissue changes during x-ray radiation therapy, chemotherapy, or other treatment; it can also be used to monitor topical application of cosmetics, skin creams, sun-blocks, or other skin treatment products.

To translate photoacoustic imaging into clinical practice, a high imaging speed is needed to reduce motion artifacts, cost, patient discomfort, and most important, the risks associated with minimally invasive procedures (e.g., endoscopy). Embodiments described herein provide the combined use of multi-focus optical illumination and ultrasonic array detection can help photoacoustic imaging meet the challenges of clinical translation. In addition, embodiments of the present disclosure uses tightly focused laser illumination to provide optical diffraction limited lateral resolution, which is difficult to achieve using ultrasonic approaches. Therefore, embodiments of the present disclosure offer a method, apparatus, and system of photoacoustic imaging with high imaging speed and spatial resolution sufficient for many clinical and preclinical applications.

FIG. 1 is a schematic of the photoacoustic probe of an imaging system 100 in accordance with one embodiment of the present disclosure, where a beam-divider, such as a 2D transmission grating, and an optically transparent acoustic reflector are employed. The light from a wavelength tunable laser is focused by a condenser lens 101 onto a pinhole 102 for spatial filtering. While a photo-detector 104 is used to monitor the laser pulse energy through a sampling beam splitter 103, an eyepiece 114 is used to optically image the object's surface for alignment. To provide multi-focus matrix illumination for photoacoustic excitation, the laser beam from the pinhole is collimated by a collimating lens 105, split by a 2D transmission grating 107, and then tightly focused by a focusing device, such as an objective lens 108, into an imaging object 111, after passing through an optically transparent acoustic reflector 110. Through an acoustic coupling medium 109 (e.g., ultrasound coupling gel), the photoacoustic signal emitted by the object is reflected by the acoustic reflector and detected by a matrix ultrasonic transducer array 112, 113. Inset A of FIG. 1 shows one possible relative positioning for the focused optical spots and the matrix ultrasonic array elements. This design is suitable for integration with commercially available ultrasonic transducer arrays (1D or 2D).

Figure 2:
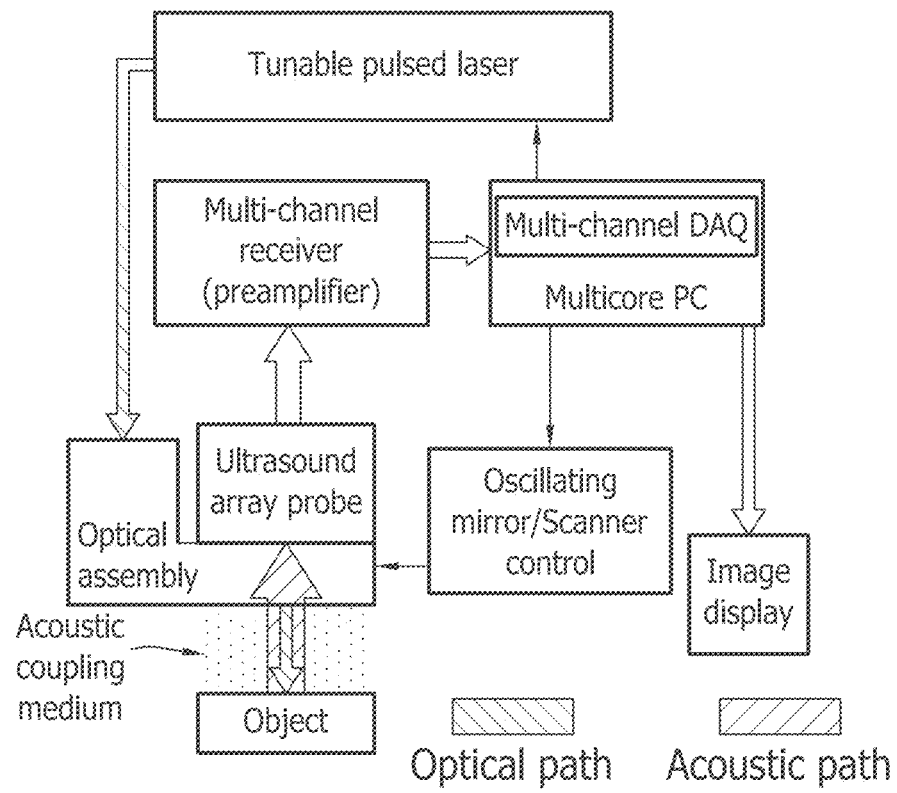
FIG. 2 is a block diagram showing the overarching architecture of the present disclosure.

FIG. 2 is a block diagram showing the overarching architecture of the present disclosure. Components include a high-repetition-rate tunable pulsed laser system, an optical assembly, an ultrasonic array, a high-speed multi-channel data acquisition (DAQ) subsystem, a scanning mirror or linear scanner, and a multi-core computer. The optical assembly receives pulsed laser light and provides multi-focus illumination for photoacoustic excitation. The DAQ system records and digitizes the received photoacoustic signal. The laser pulse generation, data acquisition, and scanning of the optical illumination are synchronized using triggering signals from the DAQ card. To optimize the data acquisition and imaging speed, the number of data acquisition channels should match the number of elements of the ultrasonic array. However, when the number of array elements is greater, multiplexers may be used. An off-the-shelf multi-core computer, together with a parallel computing program based on Microsoft Visual Studio or other software development tools, is used to perform photoacoustic reconstruction for high-speed imaging and display.

To integrate the optical focusing and the ultrasonic detection for the present disclosure, one or more of the following devices or designs can be used: (1) an optically transparent acoustic reflector; (2) an acoustically transparent optical reflector; and/or (3) direct integration in transmission mode. Examples of the integrated focusing assembly are described with reference to FIGS. 3, 4, 5, 6, 7, 8, and 9, wherein the integrated focusing assembly includes optical focusing components, a matrix ultrasonic array, and an optical-acoustic beam combiner between them.

Figure 3:
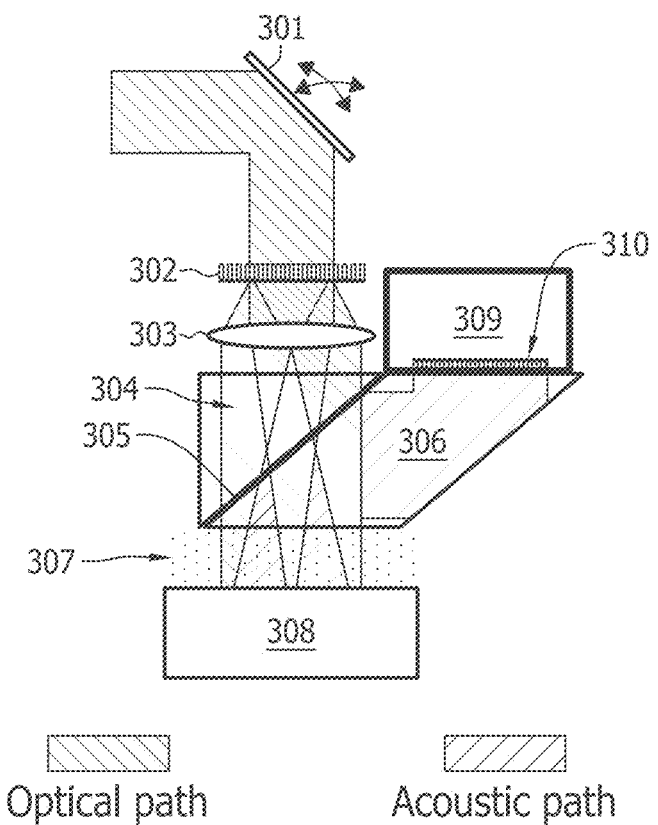
FIG. 3 is a diagram of the integrated focusing assembly of an imaging system in accordance with an alternative embodiment of the present disclosure, where a 2D transmission grating and a custom-built optical-acoustic beam combiner are employed.

FIG. 3 shows the integrated focusing assembly of an imaging system in accordance with another embodiment of the present disclosure, where a 2D transmission grating and a custom-built optical-acoustic beam combiner are employed. In this embodiment, a scanning device, such as a scanning mirror 301, is used for rapid optical scanning; the 2D transmission grating 302 is used to split the laser beams; and the optical-acoustic beam combiner 304, 305, 306 is used to merge the optical illumination and the ultrasonic detection coaxially. The optical-acoustic beam combiner mainly consists of an isosceles triangular prism 304 and a rhomboidal prism 306 (the two prisms are adjoined along the diagonal surfaces with a gap of approximately 0.1 mm in between). The gap is filled with an optical refractive-index-matching, low-acoustic-impedance, nonvolatile liquid 305 (e.g., 1000 cSt silicone oil). The silicone oil and the glass have a good optical refractive index match (glass: 1.5; silicone oil: 1.4) but a large acoustic impedance mismatch (glass: $12.1 \times 10^6$ N·s/m$^3$; silicone oil: $0.95 \times 10^6$ N·s/m$^3$). As a result, the silicone oil layer is optically transparent but acoustically reflective. The laser beams coming from the grating are tightly focused by an objective lens 303 into an imaging object 308. Through an acoustic coupling medium 307, the photoacoustic signal emitted from the object is detected by a matrix ultrasonic array 309, 310. Note that within the bandwidth of the ultrasonic array, ultrasonic absorption in the silicone oil is high enough to dampen acoustic reverberations in the matching layer and thus minimize interference with the image.

Figure 4:
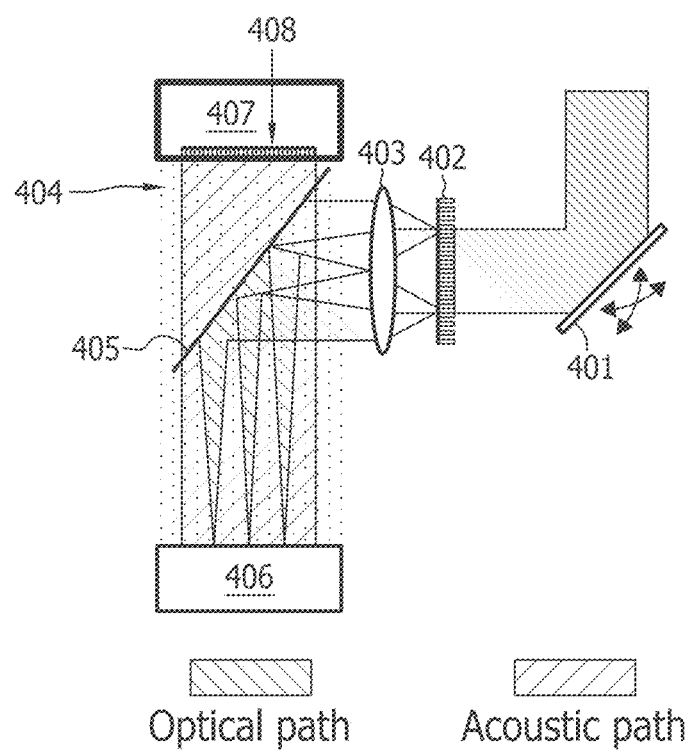
FIG. 4 is a diagram of the integrated focusing assembly of an imaging system in accordance with another alternative embodiment of the present disclosure, where a 2D transmission grating and an acoustically transparent thin-film optical reflector are employed.

FIG. 4 shows the integrated focusing assembly of an imaging system in accordance with yet another embodiment of the present disclosure, where a 2D transmission grating and an acoustically transparent thin-film optical reflector are employed. In this embodiment, a scanning mirror 401 is used for rapid optical scanning; the 2D transmission grating 402 is used to split the laser beams; and the acoustically transparent optical reflector 405 (e.g., an aluminized Mylar thin film) is used to merge the optical illumination and the ultrasonic detection coaxially. The laser beams coming from the grating are tightly focused by an objective lens 403 into an imaging object 406. Through an acoustic coupling medium 404, the photoacoustic signal emitted from the object is detected by a matrix ultrasonic array 407, 408.

Figure 5:
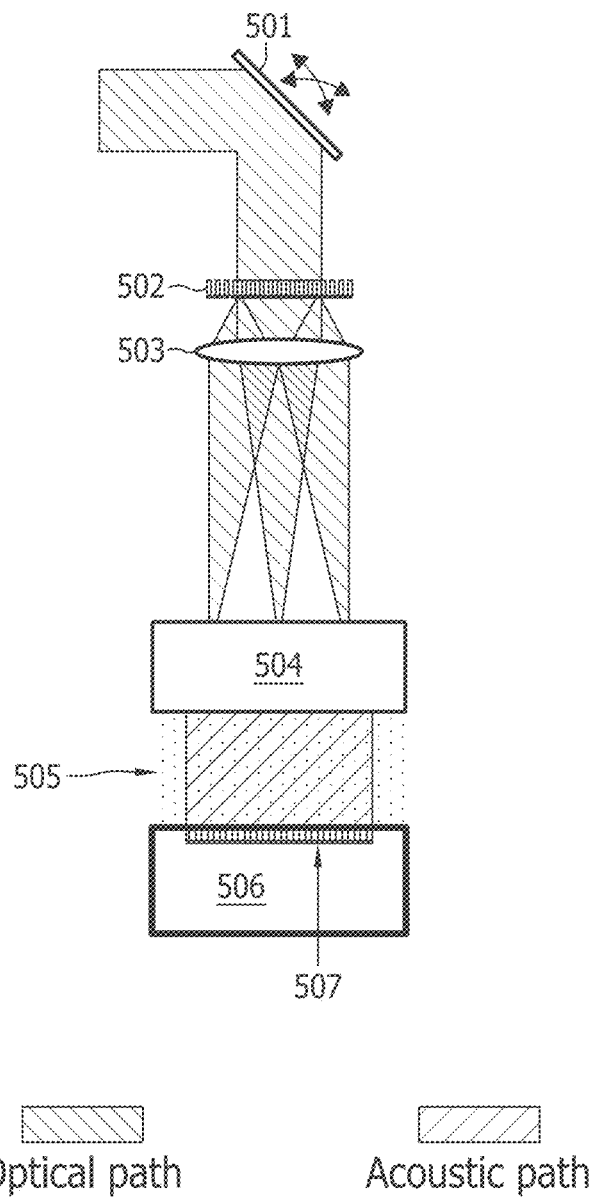
FIG. 5 is a diagram of the integrated focusing assembly of an imaging system in accordance with another alternative embodiment of the present disclosure, where a 2D transmission grating and a transmission-mode design are employed.

FIG. 5 shows the integrated focusing assembly of an imaging system in accordance with yet another embodiment of the present disclosure, where a 2D transmission grating and a transmission-mode design are employed. In this embodiment, a scanning mirror 501 is used for rapid optical scanning; the 2D transmission grating 502 is used to split the laser beams; and the transmission-mode design is used to merge the optical illumination and the ultrasonic detection coaxially. The laser beams coming from the grating are tightly focused by an objective lens 503 into an imaging object 504. From the other side of the object, through a coupling medium 505, the photoacoustic signal emitted from the object is detected by a matrix ultrasonic array 506, 507.

Figure 6:
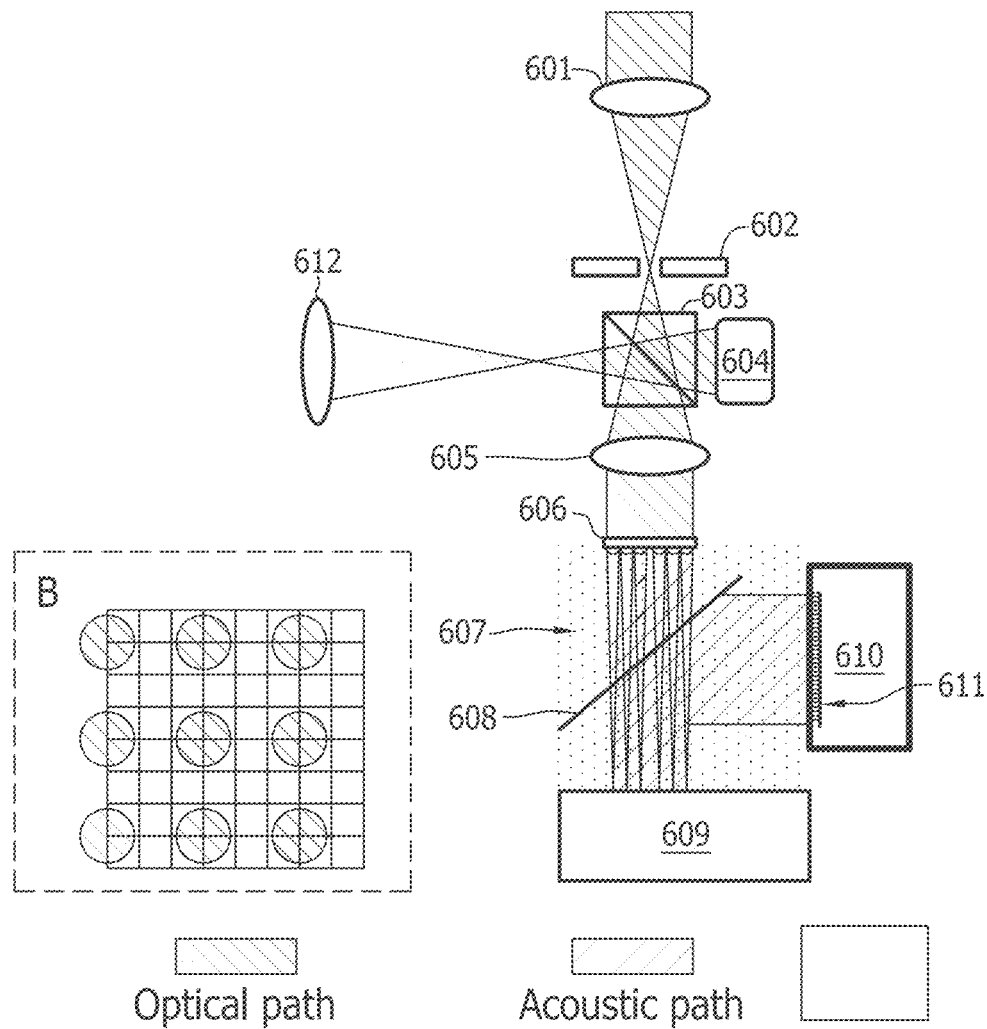
FIG. 6 is a diagram of the photoacoustic probe of an imaging system in accordance with another alternative embodiment of the present disclosure, where a 2D microlens array and an optically transparent acoustic reflector are employed.

FIG. 6 shows the photoacoustic probe of an imaging system in accordance with yet another embodiment of the present disclosure, where a 2D microlens array and an optically transparent acoustic reflector are employed. The light from a wavelength tunable laser is focused by a condenser lens 601 onto a pinhole 602 for spatial filtering. A photo-detector 604 is used to monitor the laser pulse energy through a sampling beam splitter 603, and an eyepiece 612 is used to optically image the object's surface for alignment. To provide multi-focus matrix illumination for photoacoustic excitation, the laser beam from the pinhole is first collimated by a collimating lens 605, and then split and focused by the 2D microlens array 606 into an imaging object 609, after passing through the optically transparent acoustic reflector 608. Through an acoustic coupling medium 607, the photoacoustic signal emitted from the object is reflected by the acoustic reflector and detected by a matrix ultrasonic array 610, 611. Inset B of FIG. 6 shows one possible relative positioning for the 2D microlens array and the matrix ultrasonic array. To produce a 3D image, raster scanning of the optical illumination is required, which, however, can be very fast, due to the small scanning area.

Figure 7:
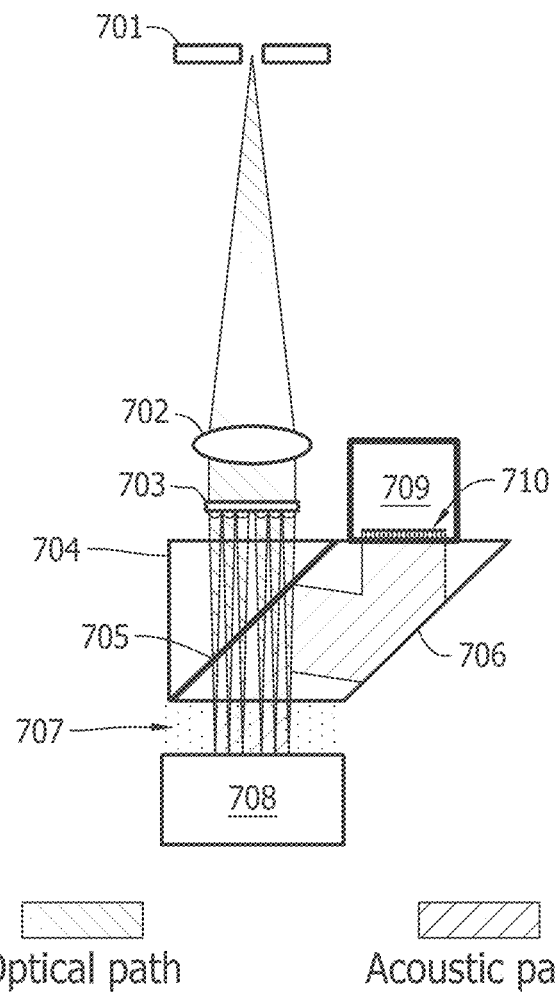
FIG. 7 is a diagram of the integrated focusing assembly of an imaging system in accordance with yet another embodiment of the present disclosure, where a 2D microlens array and a custom-built optical-acoustic beam combiner are employed.

FIG. 7 shows the integrated focusing assembly of an imaging system in accordance with yet another embodiment of the present disclosure, where a 2D microlens array and a custom-built optical-acoustic beam combiner are employed. To provide multi-focus matrix illumination for photoacoustic excitation, the laser beam from a pinhole 701 is first collimated by a collimating lens 702, and then split and focused by the 2D microlens array 703 into an imaging object 708, after passing through the optical-acoustic beam combiner 704, 705, 706. The optical-acoustic beam combiner mainly consists of an isosceles triangular prism 704 and a rhomboidal prism 706 (the two prisms are adjoined along the diagonal surfaces with a gap of approximately 0.1 mm in between). The gap is filled with an optical refractive-index-matching, low-acoustic-impedance, nonvolatile liquid 705 (e.g., 1000 cSt silicone oil). The silicone oil and the glass have a good optical refractive index match (glass: 1.5; silicone oil: 1.4) but a large acoustic impedance mismatch (glass: $12.1 \times 10^6$ N·s/m$^3$; silicone oil: $0.95 \times 10^6$ N·s/m$^3$). As a result, the silicone oil layer is optically transparent but acoustically reflective. Through an acoustic coupling medium 707, the photoacoustic signal emitted from the object is detected by a matrix ultrasonic array 709, 710. To produce a 3D image, raster scanning of the optical illumination is required, which, however, can be very fast, due to the small scanning area.

Figure 8:
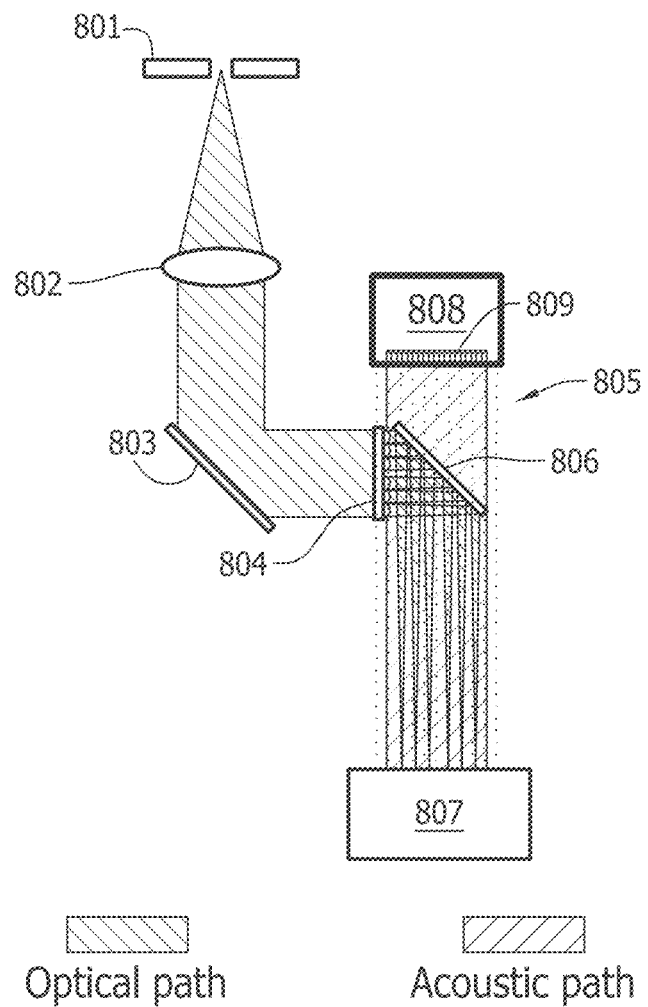
FIG. 8 is a diagram of the integrated focusing assembly of an imaging system in accordance with yet another embodiment of the present disclosure, where a 2D microlens array and an acoustically transparent thin-film optical reflector are employed.

FIG. 8 shows the integrated focusing assembly of an imaging system in accordance with yet another embodiment of the present disclosure, where a 2D microlens array and an acoustically transparent thin-film optical reflector are employed. To provide multi-focus matrix illumination for photoacoustic excitation, the laser beam from a pinhole 801 is collimated by a collimating lens 802, reflected by a dielectric mirror 803, and then split and focused by the 2D microlens array 804 into an imaging object 807. The acoustically transparent optical reflector 806 (e.g., an aluminized Mylar thin film) is used to merge the optical illumination and the ultrasonic detection coaxially. Through an acoustic coupling medium 805, the photoacoustic signal emitted from the object is detected by a matrix ultrasonic array 808, 809. To produce a 3D image, raster scanning of the optical illumination is required, which, however, can be very fast, due to the small scanning area.

Figure 9:
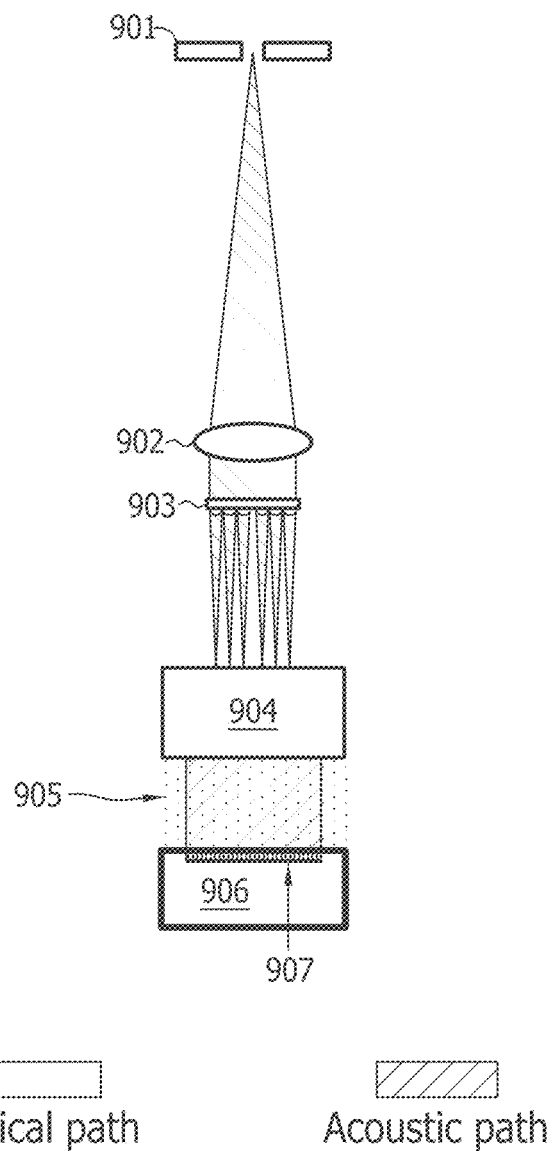
FIG. 9 is a diagram of the integrated focusing assembly of an imaging system in accordance with yet another embodiment of the present disclosure, where a 2D microlens array and a transmission-mode design are employed.

FIG. 9 shows the integrated focusing assembly of an imaging system in accordance with yet another embodiment of the present disclosure, where a 2D microlens array and a transmission-mode design are employed. The transmission-mode design is used to merge the optical illumination and the ultrasonic detection coaxially. To provide multi-focus matrix illumination for photoacoustic excitation, the laser beam from a pinhole 901 is first collimated by a collimating lens 902, and then split and focused by the 2D microlens array 903 into an imaging object 904. From the other side of the object, through a coupling medium 905, the photoacoustic signal emitted from the object is detected by a matrix ultrasonic array 906, 907. To produce a 3D image, raster scanning of the optical illumination is required, which, however, can be very fast, due to the small scanning area.

The embodiments described above are based on multi-focus matrix illumination in conjunction with matrix ultrasonic array detection. However, as mentioned above, the design can be simplified to 1D, using multi-focus 1D array illumination in conjunction with linear ultrasonic array detection. With optical scanning, this simplified design can provide real-time photoacoustic B-scan imaging, sufficient for many biomedical applications. By adding one additional mechanical scanning, 3D images can be produced at a significantly higher speed compared with mechanical scanning single-focus optical-resolution photoacoustic microscopy. In addition, the implementation of this simplified version of the present disclosure can be relatively easy and inexpensive.

The above-described embodiments have been successfully demonstrated for biomedical applications. FIG. 8 illustrates a system prototype based on the transmission mode design, and using multi-focus 1D array illumination in conjunction with linear ultrasonic array detection. The system employs a tunable dye laser pumped by an Nd:YLF laser as the irradiation source. The laser pulse duration is approximately 7 nanoseconds (ns), and the pulse repetition rate can be as high as 1.5 kHz without significant degradation of the output energy. For photoacoustic excitation, a 1D microlens array consisting of 20 micro-lenses with a center-to-center spacing of approximately 250 micrometers is used, which provides twenty focused illumination spots simultaneously. For photoacoustic signal detection, a 30-MHz linear ultrasonic array consisting of forty-eight elements with a spacing of approximately 100 micrometers is used. The system can image approximately 1 mm deep in scattering biological tissue, with finer than 10-micrometer lateral resolution and an approximately 25-micrometer axial resolution. Currently, the system acquires a volume image data set of 1000 by 500 by 200 voxels in approximately 4 min, which is about 4 times faster than existing mechanical scanning single-focus photoacoustic microscopy with optical resolution. In principle, using a 48-channel DAQ system to eliminate the 6:1 multiplexing, the system can image about 20 times faster, as determined primarily by the number of optical foci. With an increased laser repetition rate and more densely packed micro-lens array, the imaging speed of the system can be further improved. Of note, the 10-micrometer optically defined lateral resolution is one to two orders of magnitude finer than the acoustically defined counterpart, enabling the system to image capillary-level microvessels in vivo.

Figure 10A:
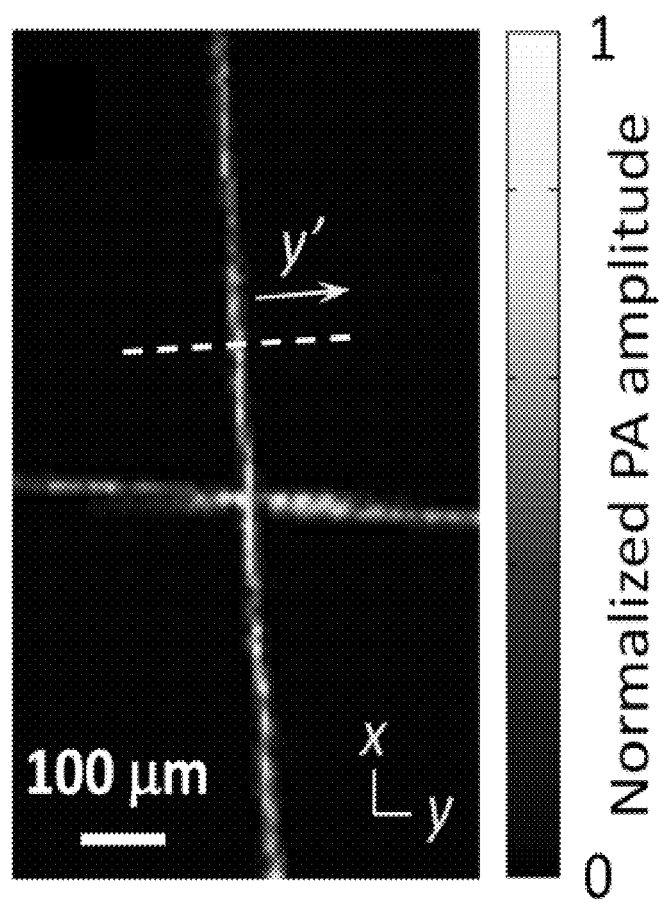
FIG. 10A shows a photoacoustic image of two crossed 6-micrometer diameter carbon fibers acquired with the current prototype of the present disclosure.
Figure 10B:
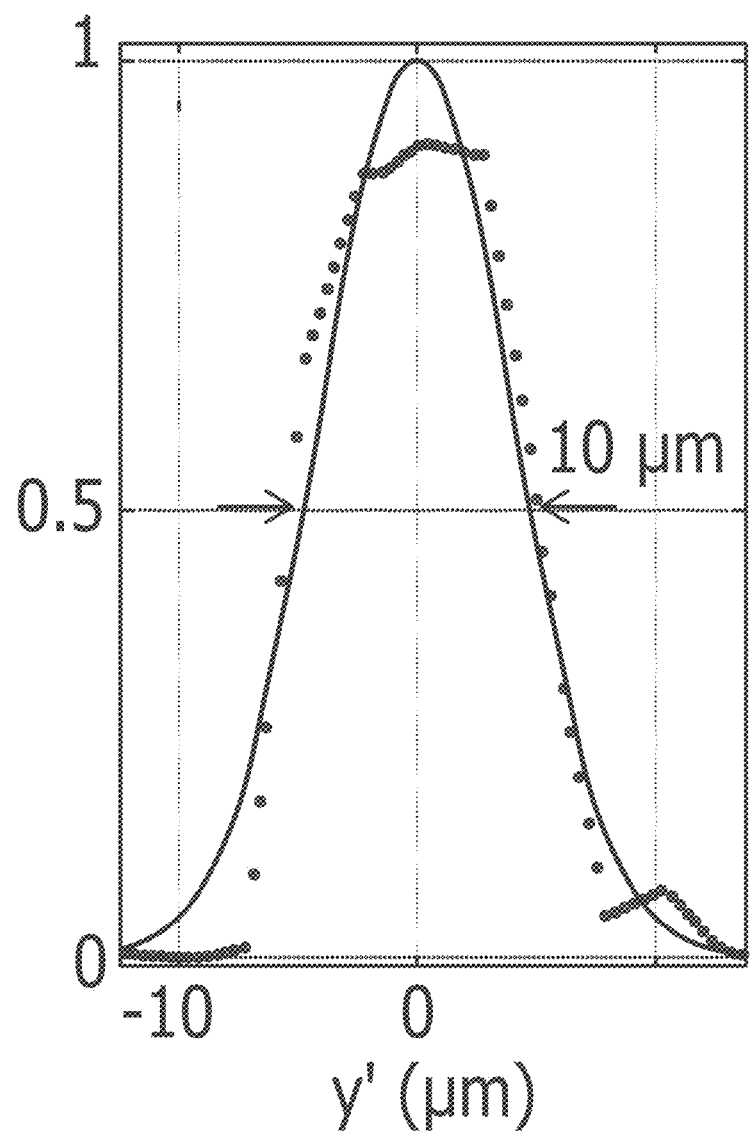
FIG. 10B shows a distribution of the photoacoustic amplitude across the vertical fiber shown in FIG. 10A.

FIG. 10A shows a photoacoustic maximum amplitude projection image of two crossed 6-micrometer diameter carbon fibers acquired at 570 nm. Maximum amplitude projection refers to projection of the maximum photoacoustic amplitudes along a direction—usually the depth or z axis direction unless otherwise mentioned—to its orthogonal plane. FIG. 10B shows the distribution of the photoacoustic amplitude across the imaged vertical fiber (along the dashed line in FIG. 10A), demonstrating that the lateral resolution of the system is at least as fine as 10 micrometers.

Figure 11A:
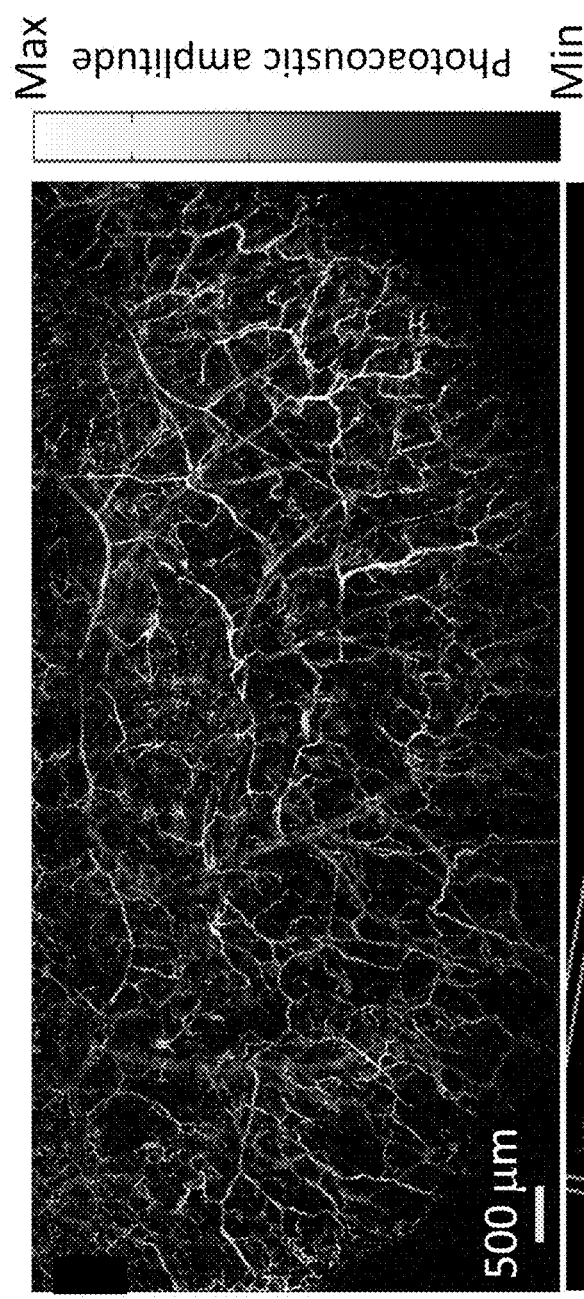
FIGS. 11A and 11B show in vivo photoacoustic images of a mouse ear vasculature acquired with the current prototype of the present disclosure.
Figure 11B:
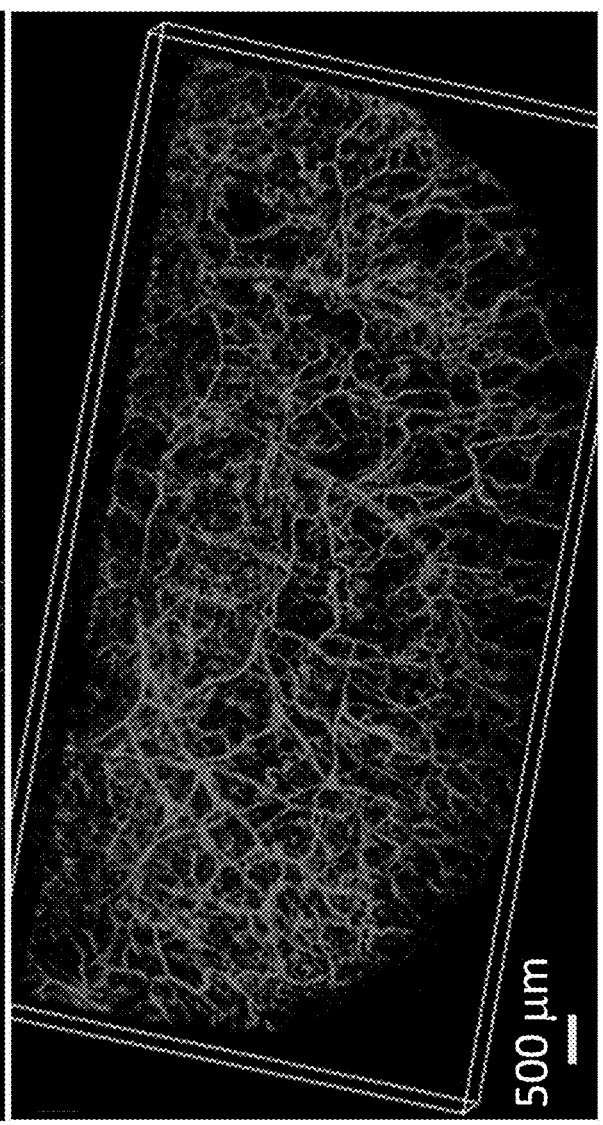

FIGS. 11A and 11B show a photoacoustic maximum amplitude projection and a 3D image of a mouse ear microvasculature, respectively, acquired noninvasively in vivo. Microvessels, including those in the capillary-level (less than approximately 10 micrometers), are clearly imaged. With high imaging speed and optically defined spatial resolution, the preliminary results demonstrate the potential of the present disclosure for broad biomedical applications. For example, imaging speed is one critical issue in advancing photoacoustic endoscopy into clinical practice for early cancer detection or intravascular atherosclerosis imaging. In addition, the high-speed, high-resolution capability will open up new possibilities for the study of tumor angiogenesis, diabetes-induced vascular complications, and pharmacokinetics.

Figure 12:
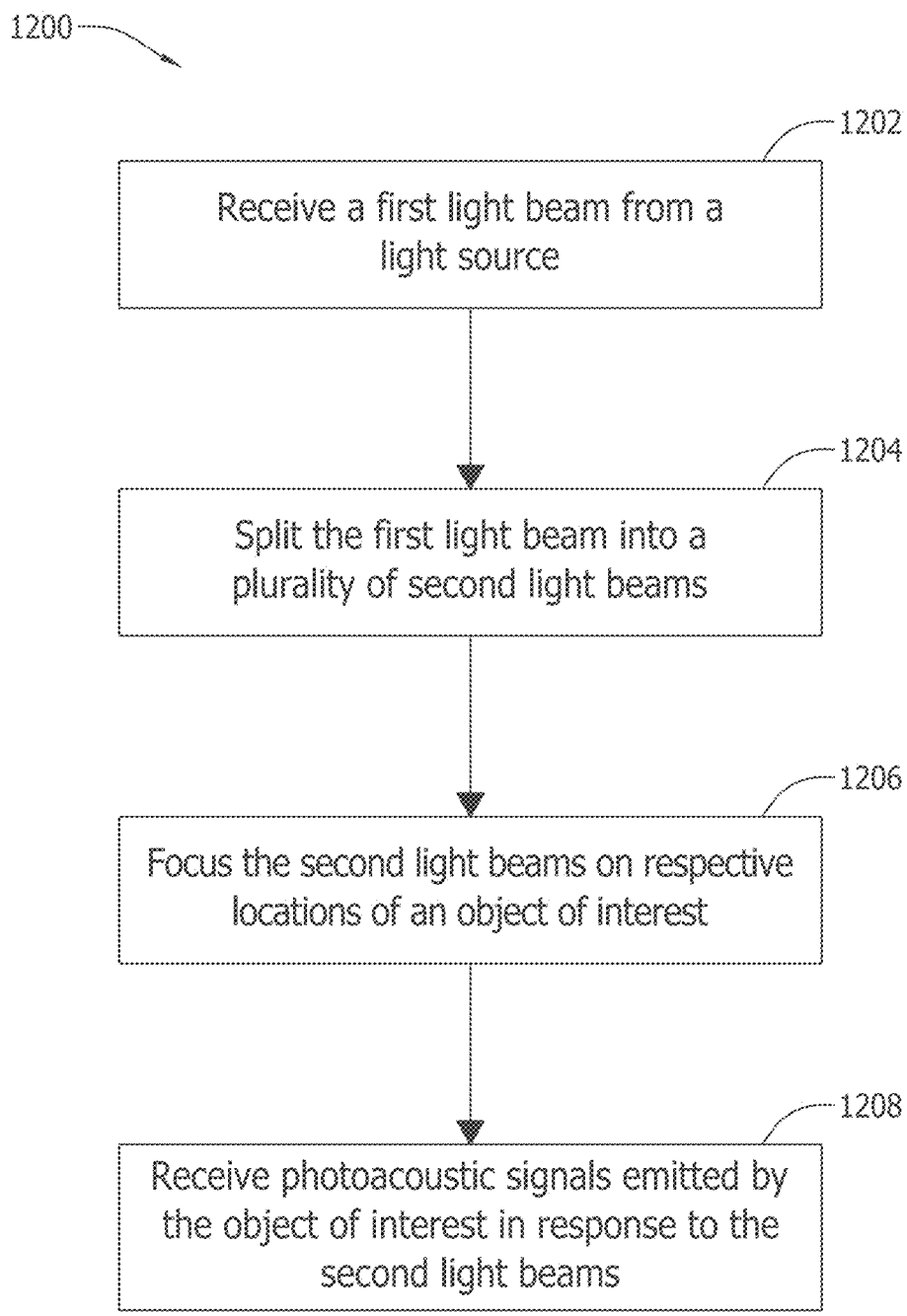
FIG. 12 is a flowchart illustrating an exemplary imaging method.

FIG. 12 is a flowchart 1200 that illustrates an exemplary imaging method. In some embodiments, a scanning device, such as scanning mirror 301, a galvanometer, a polygon scanner, an acoustic-optical scanner, and an electro-optical scanner, or another suitable scanning device, receives 1202 a first light beam from a light source, such as a laser or laser system. A beam-divider, such as transmission grating 107 or 2D microlens array 606, splits 1204 the first light beam into a plurality of second light beams. A focusing device, such as objective lens 108 or collimating lens 605, focuses 1206 the second light beams on respective locations in object of interest 111. In response to the second light beams, the temperature within object 111 at each location rises, which leads to a transient thermal expansion, resulting in emission of photoacoustic signals by object 111. The photoacoustic signals are received 1208 by ultrasonic transducer array 112, for example.

In some embodiments, a computer generates an image based on the photoacoustic signals and displays the image to an operator. Moreover, in some embodiments, the second light beams and the photoacoustic signals are coaxially merged by optical-acoustic beam combiner 304, 305, 306 that includes a first prism, such as isosceles triangular prism 304, and a second prism, such as rhomboidal prism 306, separated from first prism 304 by a gap filled with non-volatile liquid 305.

Embodiments described herein provide methods, systems, and apparatus for high-speed, optical-resolution photoacoustic imaging using multi-focus optical illumination in conjunction with ultrasonic array detection. For example, embodiments of the present disclosure use multiple focused pulsed laser beams to produce a rapid local temperature rise at multiple optical foci from absorption of the pulsed light. The temperature rise leads to a transient thermal expansion, resulting in photoacoustic emissions, which are detected by a high-frequency ultrasonic array to reconstruct an image. The image signal amplitude is related to the optical absorption and the Grueneisen parameter. With each laser pulse, the multi-focus illumination excites photoacoustic waves from multiple sites, which the ultrasonic array detects simultaneously. With an appropriate reconstruction algorithm, the signals from the multiple sites are separated. Using multi-focus matrix illumination and matrix ultrasonic array detection, a three-dimensional (3D) photoacoustic image can be produced by rapidly scanning the illumination over a small area comparable in size with the lateral resolution of the ultrasonic array. Consequently, a relatively large 3D volume (e.g., 10 mm×10 mm×1 mm) can be imaged at high speed—even in real time—with optical diffraction limited lateral resolution (e.g., 5 micrometers). In one embodiment of the present disclosure, multi-focus one-dimensional (1D) array illumination and linear ultrasonic array detection can be used. Even with this simplified design, the multi-focus optical-resolution photoacoustic microscopy device demonstrates a significant improvement in imaging speed over previous optical-resolution photoacoustic microscopy devices. Overall, embodiments of the present disclosure provide 3D photoacoustic microscopy of optical absorption contrast with optical diffraction limited lateral resolution at high speed.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations can be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present disclosure have been described in detail, it will be understood by those skilled in the art that various modifications can be made therein without departing from the spirit and scope of the disclosure as set forth in the appended claims.

A controller, computer, or computing device, such as those described herein, includes at least one processor or processing unit and a system memory. The controller typically has at least some form of computer readable media. By way of example and not limitation, computer readable media include computer storage media and communication media. Computer storage media include volatile and nonvolatile, removable and non-removable media implemented in any method or technology for storage of information such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Combinations of any of the above are also included within the scope of computer readable media.

Although the present disclosure is described in connection with an exemplary imaging system environment, embodiments of the disclosure are operational with numerous other general purpose or special purpose imaging system environments or configurations. The imaging system environment is not intended to suggest any limitation as to the scope of use or functionality of any aspect of the disclosure. Moreover, the imaging system environment should not be interpreted as having any dependency or requirement relating to any one or combination of components illustrated in the exemplary operating environment.

Embodiments of the disclosure may be described in the general context of computer-executable instructions, such as program components or modules, executed by one or more computers or other devices. Aspects of the disclosure may be implemented with any number and organization of components or modules. For example, aspects of the disclosure are not limited to the specific computer-executable instructions or the specific components or modules illustrated in the figures and described herein. Alternative embodiments of the disclosure may include different computer-executable instructions or components having more or less functionality than illustrated and described herein.

When introducing elements of aspects of the disclosure or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An imaging method, comprising:
receiving a first light beam from a light source;
splitting the first light beam into a plurality of second light beams using a beam-divider;
focusing the plurality of second light beams on respective locations in an object of interest using a focusing device, the plurality of second light beams causing the object of interest to emit acoustic signals, wherein the plurality of second light beams and the acoustic signals are coaxially aligned on opposite sides of the object of interest in a transmission mode; and
receiving the acoustic signals from the object of interest using an ultrasonic transducer array.

2. An imaging method, comprising:
  receiving a first light beam from a light source;
  splitting the first light beam into a plurality of second light beams using a beam-divider;
  focusing the plurality of second light beams on respective locations in an object of interest using a focusing device, the plurality of second light beams causing the object of interest to emit acoustic signals;
  coaxially merging the plurality of second light beams and the acoustic signals using an optical-acoustic beam combiner; and
  receiving the acoustic signals from the object of interest using an ultrasonic transducer array.

3. The imaging method of claim 2, wherein coaxially merging the plurality of second light beams and the acoustic signals comprises passing the plurality of second light beams through the optical-acoustic beam combiner to the focusing device and reflecting the acoustic signals entering the optical-acoustic beam combiner towards the ultrasonic transducer array.

4. The imaging method of claim 2, wherein coaxially merging the plurality of second light beams and the acoustic signals comprises reflecting the plurality of second light beams entering the optical-acoustic beam combiner towards the focusing device and passing the acoustic signals through the optical-acoustic beam combiner to the ultrasonic transducer array.

5. The imaging method of claim 1, further comprising reflecting the first light beam towards the beam-divider using a movable scanning mirror.

6. The imaging method of claim 5, wherein the first light beam is reflected in a raster scanning pattern.

7. The imaging method of claim 1, further comprising generating an image based on the acoustic signals.

8. The imaging method of claim 1, wherein the plurality of second light beams are formed as a linear array.

9. The imaging method of claim 1, wherein the acoustic signals are received by a linear ultrasonic transducer array.

10. The imaging method of claim 1, wherein the plurality of second light beams are formed as a 2D array.

11. The imaging method of claim 10, wherein the acoustic signals are received by a 2D ultrasonic transducer array.

12. An imaging method, comprising:
  receiving a first light beam from a light source;
  splitting the first light beam into a plurality of second light beams using a beam-divider, wherein the beam-divider comprises a transmission grating;
  focusing the plurality of second light beams on respective locations in an object of interest using a focusing device, the plurality of second light beams causing the object of interest to emit acoustic signals; and
  receiving the acoustic signals from the object of interest using an ultrasonic transducer array.

13. The imaging method of claim 1, wherein the beam-divider comprises a two-dimensional lens array.

14. The imaging method of claim 1, wherein a lens array comprises the beam-divider and the focusing device.

15. An imaging method, comprising:
  receiving a first light beam from a light source;
  splitting the first light beam into a plurality of second light beams using a beam-divider;
  focusing the plurality of second light beams on respective locations in an object of interest using a focusing device, the plurality of second light beams causing the object of interest to emit acoustic signals; and
  receiving the acoustic signals from the object of interest using an ultrasonic transducer array,
  wherein receiving the acoustic signals from the object of interest using the ultrasonic transducer array comprises simultaneously receiving a plurality of acoustic signals, each acoustic signal in the plurality of acoustic signals being emitted substantially simultaneously but from a different one of the respective locations in the object of interest.

16. An imaging system, comprising:
  a scanning device configured to steer a first light beam from a light source through a beam-divider, wherein the scanning device comprises at least one of a mechanically scanning mirror, a galvanometer, a polygon scanner, an acoustic-optical scanner, and an electro-optical scanner;
  the beam-divider configured split the first light beam into a plurality of second light beams;
  a focusing device configured to focus the plurality of second light beams onto respective locations in an object of interest being imaged, the plurality of second light beams causing the object of interest to emit acoustic signals; and
  one or more ultrasonic detection devices configured to receive the acoustic signals from the object of interest.

17. The imaging system of claim 16, wherein the beam-divider comprises a transmission grating or a two-dimensional lens array.

18. The imaging system of claim 16, wherein the beam-divider and the focusing device are part of a common array of lenses, the common array of lenses lying in a common optical plane.

* * * * *